(12) United States Patent
Wolters et al.

(10) Patent No.: US 7,436,508 B2
(45) Date of Patent: Oct. 14, 2008

(54) SYSTEMS, CIRCUITS AND METHODS FOR REDUCING THERMAL DAMAGE AND EXTENDING THE DETECTION RANGE OF AN INSPECTION SYSTEM

(75) Inventors: Christian H. Wolters, Campbell, CA (US); Anatoly Romanovsky, Palo Alto, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 126 days.

(21) Appl. No.: 11/181,228

(22) Filed: Jul. 14, 2005

(65) Prior Publication Data

US 2007/0013898 A1     Jan. 18, 2007

(51) Int. Cl.
*G01N 21/00* (2006.01)
(52) U.S. Cl. .................... 356/237.5; 356/237.4
(58) Field of Classification Search ... 356/237.1–237.5, 356/236, 51; 250/207, 214 L, 214 R, 363.01, 250/205
See application file for complete search history.

(56) References Cited

U.S. PATENT DOCUMENTS

| | | | |
|---|---|---|---|
| 3,488,434 A | 1/1970 | Farber | |
| 3,997,779 A | 12/1976 | Rabl | |
| 4,048,510 A | 9/1977 | Clarke et al. | |
| 4,767,211 A | 8/1988 | Munakata et al. | |
| 4,806,776 A | 2/1989 | Kley | |
| 5,076,692 A | 12/1991 | al. | |
| 5,793,230 A | 8/1998 | Chu et al. | |
| 5,860,972 A | 1/1999 | Hoang | |
| 6,002,122 A | 12/1999 | Wolf | |
| 6,188,473 B1 | 2/2001 | Wolf et al. | |
| 6,348,682 B1 | 2/2002 | Lee | |
| 6,448,064 B1 | 9/2002 | Vo-Dinh et al. | |
| 6,621,571 B1 | 9/2003 | Maeda et al. | |
| 6,833,913 B1 | 12/2004 | Wolf et al. | |
| 7,109,463 B2 | 9/2006 | Milshtein et al. | |
| 2002/0043109 A1 | 4/2002 | Siu | |
| 2002/0043614 A1 | 4/2002 | Miyamoto et al. | |
| 2003/0047667 A1 | 3/2003 | Filkins et al. | |
| 2003/0058433 A1 | 3/2003 | Almogy et al. | |

(Continued)

OTHER PUBLICATIONS

International Search Report and Written Opinion for PCT Application No. PCT/US06/27129 dated Jun. 17, 2007.

*Primary Examiner*—Gregory J. Toatley, Jr.
*Assistant Examiner*—Tri T Ton
(74) *Attorney, Agent, or Firm*—Baker & McKenzie LLP

(57) ABSTRACT

Inspection systems, circuits, and methods are provided to enhance defect detection by reducing thermal damage to large particles by dynamically altering the incident laser beam power level supplied to the specimen during a surface inspection scan. In one embodiment, an inspection system includes an illumination subsystem for directing light to a specimen at a first power level, a detection subsystem for detecting light scattered from the specimen, and a power attenuator subsystem for dynamically altering the power level directed to the specimen based on the scattered light detected from the specimen. For example, the power attenuator subsystem may reduce the directed light to a second power level, which is lower than the first, if the detected scattered light exceeds a predetermined threshold level. In addition reducing thermal damage, the systems and methods described herein may be used to extend the measurement detection range of an inspection system by providing a variable-power inspection system.

19 Claims, 9 Drawing Sheets

U.S. PATENT DOCUMENTS

| | | |
|---|---|---|
| 2003/0174324 A1 | 9/2003 | Sandstrom |
| 2004/0016867 A1 | 1/2004 | Milshtein et al. |
| 2004/0054303 A1 | 3/2004 | Taylor |
| 2004/0095573 A1 * | 5/2004 | Tsai et al. ............... 356/237.5 |
| 2004/0198028 A1 | 10/2004 | Tanaka et al. |
| 2005/0092899 A1 * | 5/2005 | Wolf et al. .............. 250/214 R |
| 2006/0066843 A1 | 3/2006 | Guetta et al. |
| 2007/0012867 A1 | 1/2007 | Wolters et al. |
| 2007/0013899 A1 | 1/2007 | Wolters et al. |

* cited by examiner

SYSTEMS, CIRCUITS AND METHODS FOR REDUCING THERMAL DAMAGE AND EXTENDING THE DETECTION RANGE OF AN INSPECTION SYSTEM

BACKGROUND OF THE INVENTION

1. Field of the Invention

The present invention generally relates to circuits, systems and methods for inspecting a specimen. In particular, the present invention relates to circuits, systems and methods for reducing thermal damage to large particles by dynamically altering the incident laser beam power level supplied to the specimen during a surface inspection scan. In addition, the systems and methods described herein may be used to extend the measurement detection range of an inspection system by providing a variable-power inspection system.

2. Description of the Related Art

Fabricating semiconductor devices, such as logic, memory and other integrated circuit devices, typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process, and thus, higher profits. Inspection has always been an important part of semiconductor fabrication. However, as the dimensions of semiconductor devices decrease, inspection becomes even more important to the successful manufacture of acceptable semiconductor devices. For instance, detecting defects of decreasing size has become increasingly necessary, since even relatively small defects may cause unwanted aberrations in the semiconductor device, and in some cases, may cause the device to fail.

Many different types of inspection tools have been developed for the inspection of semiconductor wafers, including optical and E-beam systems. Optical inspection tools may be generally characterized into dark-field and bright-field inspection systems. Dark-field systems are typically known for having a relatively high detection range. For instance, dark-field systems detect the amount of light that is scattered from the surface of a specimen when an incident beam is supplied to the specimen at a normal or oblique angle. The amount of scattered light detected by the system generally depends on the optical characteristics of the spot under inspection (e.g., the refractive index of the spot), as well as any spatial variations within the spot (e.g., uneven surface topologies). In the case of dark-field inspection, smooth surfaces lead to almost no collection signal, while surfaces with protruding features (such as patterned features or defects) tend to scatter much more strongly (sometimes up to six orders of magnitude or more). Bright-field inspection systems direct light to a specimen at a particular angle and measure the amount of light reflected from the surface of the specimen at a similar angle. In contrast to dark-field systems, the variations in the reflected signal collected by a bright-field system are generally no more than about two orders of magnitude.

In addition, most inspection tools are designed to inspect either unpatterned or patterned semiconductor wafers, but not both. Since the tools are optimized for inspecting a particular type of wafer, they are generally not capable of inspecting different types of wafers for a number of reasons. For example, many unpatterned wafer inspection tools are configured such that all of the light collected by a lens (or another collector) is directed to a single detector that generates a single output signal representative of all of the light collected by the lens. Therefore, light scattered from patterns or features on a patterned wafer will be combined with other scattered light (e.g., from defects). In some cases, the single detector may become saturated, and as a result, may not yield signals that can be analyzed for defect detection. Even if the single detector does not become saturated, the light scattered from patterns or other features on the wafer cannot be separated from other scattered light thereby hindering, if not preventing, defect detection based on the other scattered light.

Tools used for inspecting patterned wafers generally employ at least two detectors for improved spatial resolution. However, the detectors used in patterned wafer inspection tools may also become saturated, especially when imaging with a dark-field system. As noted above, dark-field scattering signals obtained from a patterned wafer may vary by six orders of magnitude (or more) due to the variation in surface topology from smooth surface regions (which appear dark) to highly textured regions (which appear bright). It is often difficult, especially with detection systems operating at high data rates, to collect meaningful signals from both the very dark and the very bright areas of the substrate being inspected without "on-the-fly" adjustment.

Most optical inspection tools are limited in either detection range, detection sensitivity, or both. For example, inspection tools employing high-gain detectors to obtain higher detection range may be incapable of detecting smaller (i.e., low light) signals. On the other hand, inspection tools with lower-gain detectors may achieve greater sensitivity at the cost of reduced detection range. In other words, although lower gain detectors may be capable of detecting smaller signals, they may become saturated when larger signals are received. Other factors tend to limit the detection range, in addition to detector gain. For example, further limitations may be imposed by the amplification circuitry or the fast analog-to-digital converters used to convert the scattered output signals into a format suitable for signal processing.

One possible solution to this problem is to apply non-linear amplification to the output signal of a detector, in order to emphasize the low-amplitude signal range. An approach of this sort is described by Wolf in U.S. Pat. No. 6,002,122, whose disclosure is herein incorporated by reference. In the method described by Wolf, the output signal from a photomultiplier tube (PMT) is processed by a logarithmic amplifier and gain correction mechanism. Wolf emphasizes the low-amplitude signal range by changing the PMT gain "on-the-fly" (by changing the bias potentials supplied to the dynodes) to avoid anode saturation, a common detection range limitation of PMT detectors. Although this approach may provide improved visibility of small-signal defects in the dark-field image, it does nothing to extend the overall detection range of the inspection system. In addition, the "on-the-fly" gain modulation disclosed by Wolf causes the PMT to be operated in a highly non-linear way, thus requiring complex (and expensive) drive electronics and sophisticated calibrations to compensate for the non-linear and transient effects.

Another approach to extend the detection range of an inspection system is to utilize two or more detectors with separate detection channels. An approach of this sort is described by Almogy et al. in U.S. Patent Application No. 2003/0058433, whose disclosure is herein incorporated by reference. Almogy describes a defect detection system that utilizes at least two detectors. One of the detectors is optimized for high sensitivity, while the other is designed to have a high saturation level, typically at the expense of sensitivity. The light scattered from a specimen is split among the detectors with the addition of various optical components. Though Almogy is able to extend the detection range, Almogy does so by requiring multiple detectors with additional optics and electronic circuitry, all of which consume additional space, increase complexity, and incur higher cost.

Therefore, a need remains for improved circuits and methods for extending the detection range of a wafer inspection system. Preferably, such improved circuits and methods would provide significant measurement range extension without the complexity and cost of real-time gain adjustment, as required by Wolf, or the additional detectors, optics and electronic circuitry required by Almogy. In addition, an improved inspection system would extend the detection range without sacrificing throughput or sensitivity. In some cases, the improved inspection system may be used for inspecting both patterned and unpatterned wafers.

SUMMARY OF THE INVENTION

The following description of various embodiments of systems, circuits and methods is not to be construed in any way as limiting the subject matter of the appended claims.

The inspection systems, circuits and methods described herein enhance defect detection by reducing thermal damage to large particles by dynamically altering the incident beam power level before scanning over such particles. In addition to reducing thermal damage, the circuits, systems and methods described herein may be used to extend the measurement detection range of an inspection system by providing a variable-power inspection system. Other advantages will become apparent upon reading this disclosure.

In accordance with one embodiment of the invention, an inspection system may include an illumination subsystem for directing light to a specimen at a first power level, a detection subsystem for detecting light scattered from the specimen, and a power attenuator subsystem for dynamically altering the power level directed to the specimen based on the scattered light detected from the specimen.

In some cases, the power attenuator subsystem may include a laser power attenuator arranged between the light source and the specimen. In such cases, the laser power attenuator may be configured to maintain the light directed to the specimen at the first power level, if the detected scattered light remains below a predetermined threshold level, or reduce the light directed to the specimen to a second power level, which is less than the first, if the detected scattered light exceeds the predetermined threshold level. In some cases, the laser power attenuator may be configured to increase the light directed to the specimen (e.g., back to the first power level), if the detected scattered light falls back below the predetermined threshold level.

In some cases, the power attenuator subsystem may also include a laser power controller coupled between the detection subsystem and the laser power attenuator. In such cases, the laser power controller may be configured to continuously monitor the detected scattered light to determine whether the detected scattered light is above or below the predetermined threshold level. Based on such determination, the laser power controller may instruct the laser power attenuator to provide the light directed to the specimen at either the first power level or the second power level.

In general, the predetermined threshold level may be set (e.g., by a user or processing component of the system) to reduce or prevent thermal damage, which is often caused when the light directed to the specimen is absorbed and inadequately dissipated by a feature on the specimen (such as a large particle or defect). The predetermined threshold level is typically based on an incident laser power density associated with the onset of thermal damage inflicted on a feature of certain size. In one example, the predetermined threshold level may be selected from a group of incident laser power densities ranging, e.g., from about 1 kW/cm$^2$ to about 1000 kW/cm$^2$, to avoid damaging relatively large particles (e.g., >5 µm) on the specimen.

In general, the second power level will be substantially lower than the first power level to avoid damaging large particles when an incident laser beam is supplied thereto. For example, the second power level may be selected as a percentage (e.g., about 1% to about 50%) of the first power level. In one embodiment, the second power level may be substantially equal to about 10% of the first power level. Other power levels may be used, as desired. In this manner, the inspection system described herein may be configured to detect features of relatively small size by directing the light to the specimen at the first power level. In addition, the inspection system may also detect features of relatively larger size, without inflicting thermal damage on those features, by directing the light to the specimen at the second power level, rather than the first.

In accordance with another embodiment of the invention, a method is described herein for inspecting a specimen under observation. In general, the method may include directing light to the specimen at a first power level, while scanning the light over a surface of the specimen. While scanning, the method may detect light scattered from the specimen, so that features, defects or light scattering properties of the specimen may be detected. In some cases, the light directed to the specimen (i.e., an incident laser beam) may be reduced to a second power level, if the detected light exceeds a predetermined threshold level. In such a case, the directed light may be subsequently increased (e.g., back up to the first power level), if the detected scattered light falls back below the predetermined threshold level during said scanning.

In one embodiment, the light directed to the specimen may be supplied to a surface of the specimen with a power density distribution that peaks near the middle of the distribution and tapers off near the edges of the distribution. As used herein, the middle of the distribution may be referred to as the "main beam," while the edges of the distribution are referred to as the "beam skirt." As an example, the power density distribution may include a Gaussian distribution with one main lobe and a gradually tapered beam skirt. However, other appropriately shaped distributions may be used, as desired.

In addition to detecting the scattered light, the method may also monitor the light scattered from the specimen during said scanning. For example, a separate photodetector may be included to monitor the light scattered from the specimen, in some embodiments of the invention. If a separate detector is included, the method may use the monitored light to select a particular threshold level, which may then be used for selecting an appropriate power level to be directed to the specimen. However, the monitoring step may not be used in all embodiments of the invention.

By monitoring scatter levels, the method described herein may reduce an incident laser beam to a lower power level (e.g., the second power level) before the main beam reaches a relatively large feature on the specimen. In other words, thermal damage may be reduced or avoided by dynamically reducing the power level supplied to a feature, which would otherwise be susceptible to thermal damage if the main beam were supplied thereto at a higher power level (e.g., the first power level). In addition, the method described herein maintains throughput and sensitivity of the inspection system by adjusting the incident laser beam power level "on-the-fly."

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
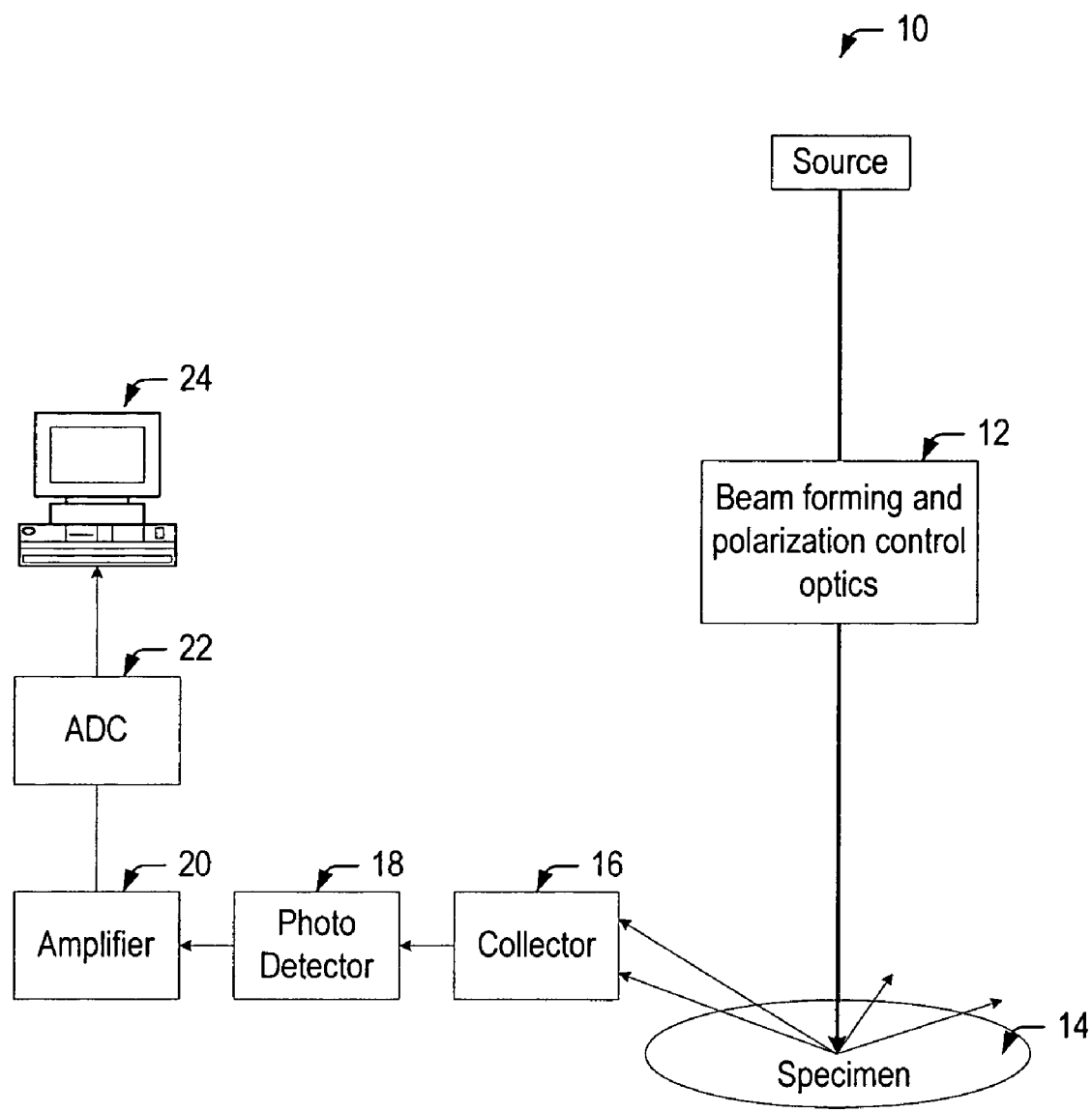
FIG. 1 is a block diagram of an exemplary inspection system including an illumination subsystem for directing light towards a specimen, a detection subsystem for detecting light scattered from the specimen, and a processor for detecting features, defects or light scattering properties of the specimen using the detected light.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The methods and systems described herein enhance defect detection by addressing various limiting factors of measurement detection range including, but not limited to, detector saturation, amplifier saturation and the fixed bit range of analog-to-digital converters (ADC). Unlike some currently used inspection methods, the inspection system described herein is able to extend the measurement detection range while maintaining signal linearity and stability, and without employing additional detectors, optics and electronic components, all of which undesirably increase space consumption, complexity and cost of the inspection system.

Various embodiments are described herein for an optical inspection system or tool that may be used for inspecting a specimen. The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

In some cases, a wafer may include only the substrate, such as a virgin wafer. Alternatively, a wafer may include one or more layers that may be formed upon a substrate. Examples of such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials, such as "xerogels," and "high-k" dielectric materials, such as tantalum pentoxide. In addition, examples of conductive materials may include, but are not limited to, aluminum, polysilicon, and copper.

One or more layers formed on a wafer may be "patterned" or "unpatterned." For example, a wafer may include a plurality of dies having repeatable pattern features. Formation and processing of such layers of material may ultimately result in completed semiconductor devices. As such, a wafer may include a substrate on which not all layers of a complete semiconductor device have been formed, or a substrate on which all layers of a complete semiconductor device have been formed. The term "semiconductor device" may be used interchangeably herein with the term "integrated circuit." In addition, other devices such as microelectromechanical (MEMS) devices and the like may also be formed on a wafer.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

Turning now to the drawings, it is noted that FIGS. 1, 2, 4, 5, and 7-10 are not drawn to scale. In particular, the scale of some of the elements of the figures are greatly exaggerated to emphasize characteristics of the elements. It is also noted that FIGS. 1, 2, 4, 5, and 7-10 are not drawn to the same scale. Similar elements shown in more than one figure have been indicated using the same reference numerals.

FIG. 1 illustrates a system that may be used to perform the inspection methods described herein. The system shown in FIG. 1 illustrates a general optical configuration that can be used to inspect a specimen according to the methods described herein. The inspection system includes a dark-field optical subsystem. It will be obvious to one of ordinary skill in the art that the illustrated system may be altered in many ways while still providing the capability to perform the methods described herein. In addition, it will be obvious to one of ordinary skill in the art that the illustrated system may include various additional components that are not shown in FIG. 1 such as a stage, a specimen handler, folding mirrors, polarizers, additional light sources, additional collectors, etc. All such variations are within the scope of the invention described herein.

The system illustrated in FIG. 1 includes an illumination subsystem. The illumination subsystem is configured to direct light to a specimen. For example, the illumination subsystem includes light source 10. Light source 10 may include, for example, a laser, a diode laser, a helium neon laser, an argon laser, a solid state laser, a diode pumped solid state (DPSS) laser, a xenon arc lamp, a gas discharging lamp, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 mm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

The illumination subsystem also includes various beam forming and polarization control optics 12. For example, the illumination subsystem may include various optics for directing and supplying an incident beam to specimen 14 with, e.g., a particular spot size. If the light source is configured to emit light of various polarizations, the illumination subsystem may also include one or more polarizing components that may alter the polarization characteristics of the light emitted by the light source. In some cases, the light directed to specimen 14 may be coherent or incoherent. The beam forming and polarization control optics 12 may include a number of components, which are not shown in FIG. 1, such as a beam expander, folding mirrors, focusing lenses, cylindrical lenses, beam splitters, etc.

In some cases, the illumination subsystem may include a deflector (not shown). In one embodiment, the deflector may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

As shown in FIG. 1, the illumination subsystem may be configured to direct the beam of light to the specimen at a normal angle of incidence. In this embodiment, the illumination subsystem may not include a deflector since the normal incidence beam of light may be scanned over the specimen by relative motion of the optics with respect to the specimen and/or by relative motion of the specimen with respect to the optics. Alternatively, the illumination subsystem may be configured to direct the beam of light to the specimen at an oblique angle of incidence. The system may also be configured to direct multiple beams of light to the specimen such as an oblique incidence beam of light and a normal incidence beam of light. The multiple beams of light may be directed to the specimen substantially simultaneously or sequentially.

The inspection system of FIG. 1 includes a single collection channel. For example, light scattered from the specimen may be collected by collector 16, which may be a lens, a compound lens, or any appropriate lens known in the art. Alternatively, collector 16 may be a reflective or partially reflective optical component, such as a mirror. In addition, although one particular collection angle is illustrated in FIG. 1, it is to be understood that the collection channel may be arranged at any appropriate collection angle. The collection angle may vary depending upon, for example, the angle of incidence and/or topographical characteristics of the specimen.

The inspection system also includes a detector 18 for detecting the light scattered from the specimen and collected by collector 16. Detector 18 generally functions to convert the scattered light into an electrical signal, and therefore, may include substantially any photodetector known in the art. However, a particular detector may be selected for use within one or more embodiments of the invention based on desired performance characteristics of the detector, the type of specimen to be inspected and/or the configuration of the illumination subsystem. For example, if the amount of light available for inspection is relatively low, an efficiency enhancing detector such as a time delay integration (TDI) camera may increase the signal-to-noise ratio and throughput of the system. However, other detectors such as charge-coupled device (CCD) cameras, photodiodes, phototubes and photomultiplier tubes (PMTs) may be used, depending on the amount of light available for inspection and the type of inspection being performed. In at least one embodiment of the invention, a photomultiplier tube is used for detecting light scattered from a specimen.

The inspection system also includes various electronic components needed for processing the scattered signals detected by detector 18. For example, the system shown in FIG. 1 includes amplifier circuitry 20, analog-to-digital converter (ADC) 22 and processor 24. Amplifier 20 is generally configured to receive output signals from detector 18 and to amplify those output signals by a predetermined amount. ADC 22 converts the amplified signals into a digital format suitable for use within processor 24. In one embodiment, the processor may be coupled directly to ADC 22 by a transmission medium, as shown in FIG. 1. Alternatively, the processor may receive signals from other electronic components coupled to ADC 22. In this manner, the processor may be indirectly coupled to ADC 22 by a transmission medium and any intervening electronic components.

In general, processor 24 is configured for detecting features, defects, or light scattering properties of the specimen using electrical signals obtained from the single collection channel. The signals produced by the single collection channel are representative of the light detected by a single detector (detector 18). The term "single detector" may be used herein to describe a detector having only one sensing area, or possibly several sensing areas (such as found, e.g., in a detector array or multi-anode PMT). Regardless of number, the sensing areas of a single detector are embodied within a single enclosure. In some cases, the inspection system described herein may be used for inspecting patterned, as well as unpatterned specimens. The processor may include any appropriate processor known in the art. In addition, the processor may be configured to use any appropriate defect detection algorithm or method known in the art. For example, the processor may use a die-to-database comparison or a thresholding algorithm to detect defects on the specimen.

The inspection system described herein provides more features, defects, or light scattering property information about specimens than other inspection systems, which trade-off detection range for sensitivity (or vice versa). In other words, the inspection system described herein provides extended detection range (e.g., about 0 to about 3 orders of magnitude, or more) without sacrificing sensitivity. The improved inspection system also maintains excellent signal linearity and stability, and does not require complex calibrations or additional detectors and optics to extend the detection range. The improved inspection system achieves all this by addressing several factors, which tend to limit the detection range of an inspection system. These factors include, but are not limited to, detector saturation, amplifier saturation and the fixed bit range of analog-to-digital converters. The limitations set by detector saturation will now be described in the context of photomultiplier tubes. It is recognized, however, that the general concepts outlined below may be applicable to other types of detectors.

Photomultiplier tubes (PMTs) are often used as detectors when optical signals are dim (i.e., in low-intensity applications, such as fluorescence spectroscopy). A typical photomultiplier tube consists of a photoemissive cathode (photocathode) followed by focusing electrodes, a plurality of dynodes (forming an electron multiplier) and an anode (forming an electron collector) in a vacuum tube. When light enters the PMT, the photocathode emits photoelectrons into the vacuum. The focusing electrodes direct the photoelectrons towards the electron multiplier where electrons are multiplied by the process of secondary emission. For example, the photoelectrons are accelerated from the photocathode to the first dynode by an electric field. When they strike the dynode, they dislodge additional electrons to amplify the photoelectric signal. These secondary electrons cascade towards the next dynode where they are again amplified. At the end of the dynode chain, the electrons are collected by the anode to generate an electrical output signal in proportion to the amount of light entering the PMT. The output signal produced at the anode is generally large enough to be measured using conventional electronics, such as a transimpedance amplifier followed by an analog-to-digital converter.

The process of secondary emission enables the photomultiplier tube to achieve high current amplification. In other words, a very small photoelectric current from the photocathode can be observed as a large output current from the anode of the photomultiplier tube. Current amplification (otherwise referred to as gain) is simply the ratio of the anode output current to the photoelectric current from the photocathode. The gain at each dynode is a function of the energy of the incoming electrons, which is proportional to the electric potential between that dynode and the previous stage. The total gain of the PMT is the product of the gains from all of the dynode stages. When a voltage (V) is applied between the cathode and the anode of a photomultiplier tube having (n) dynode stages, the total gain becomes:

$$G(V) \propto V^{\alpha n} \qquad \text{EQ. 1}$$

where, $\alpha$ is a coefficient determined by the dynode material and geometric structure (typically in the range of 0.6 to 0.8).

In most cases, a photomultiplier tube will be operated at a single predetermined gain. For example, bias voltages may be generated for each of the dynodes by connecting a string of voltage-divider resistors between the cathode, all of the dynodes, the anode and ground. The resistance, R, is used as a scaling constant and is typically the same for all stages of the photomultiplier tube. A large negative voltage (typically −500 V to −1500 V) is then applied to the cathode, and the potential is divided up evenly across the dynodes by the voltage-divider resistor chain. Doing so enables each of the dynodes to be maintained at successively less negative potentials, the difference between which establishes the intermediate dynode gain. Though the total gain of the photomultiplier tube may be altered by changing the voltage applied to the cathode, it is generally not desirable to do so. For example, the large voltages involved make it difficult to change the gain quickly, due to parasitic capacitances and the large resistor values needed to limit power dissipation in the bias string. Therefore, most users decide on a tube gain in advance, set the appropriate cathode voltage and then operate the tube at that voltage throughout the measurement operations.

In this configuration, the detection range of the photomultiplier tube is limited on the low end by the noise and gain characteristics of the transimpedance amplifier and, on the high end, by the ability of the photomultiplier tube to deliver anode current. In low-intensity applications, the anode current is limited by space charge effects within the tube, bias string power consumption, and the consumable nature of the material coating the dynodes. In high-intensity applications, the photomultiplier tube is limited by saturation of the anode, and sometimes, the cathode. For example, the photomultiplier tube may provide inaccurate results when relatively large amounts of light cause the anode (or cathode) to become saturated. In the following embodiments, the present invention addresses anode saturation as a limiting factor to the detection range of an inspection system. As described in more detail below, the present invention avoids measurement inaccuracies and extends the detection range of a PMT detector by providing circuits and methods designed, in one aspect, for avoiding anode saturation.

Figure 2A:
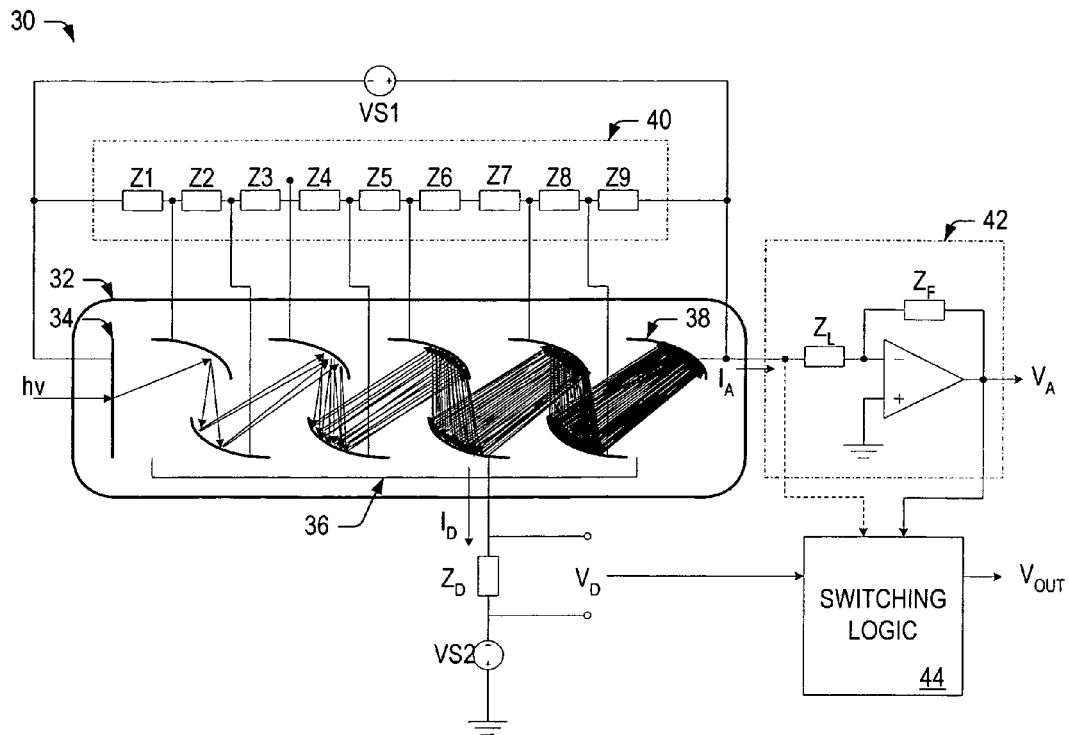
FIG. 2A is a block diagram of an exemplary circuit included within the detection subsystem of FIG. 1 for detecting the light scattered from the specimen, according to a first embodiment of the invention.

FIG. 2A illustrates one embodiment of a circuit 30 that may be used for detecting light scattered from a specimen. As such, circuit 30 may be incorporated within the inspection system of FIG. 1 as detector 18. In the embodiment of FIG. 2A, circuit 30 includes a photomultiplier tube (PMT) 32 having a cathode 34, a plurality of dynodes 36 and an anode 38. Though shown having only 8 dynodes, PMT 32 may include substantially any appropriate number of dynodes, with typical numbers ranging between about 8 and about 20. PMT 32 is also illustrated in FIG. 2A as a head-on photomultiplier tube, and in particular, a linear-focused head-on PMT operated in a transmission mode. However, one of ordinary skill in the art would recognize how the inventive aspects described herein may be applied to other modes and/or types of PMTs. For example, PMT 32 may be alternatively formed in a side-on configuration and/or operated in reflection mode. In addition to the linear-focused PMT shown in FIG. 2A, the inventive aspects could be applied to other types of PMTs including, but not limited to, circular-cage type, box-and-grid type, Venetian blind type, and mesh type.

Like conventional PMT circuits, circuit 30 includes a voltage-divider chain 40 with impedance elements (e.g., Z1-Z9) coupled across the cathode, most of the dynodes and the anode. The impedance elements may include resistors of equal resistance, a tapered resistance, or even a combination of resistors and capacitors, as is known in the art. Therefore, when a high negative voltage ($V_{S1}$) is applied to the cathode, the potential may be divided up evenly across all of the dynodes, or somewhat unevenly so that dynodes in the middle of the chain experience less gain. When light (hv) enters the PMT, cathode 34 emits photoelectrons which cascade through dynode chain 36 to produce an amplified photoelectric current ($I_A$) at anode 38. The current output from anode 38 is converted into a voltage ($V_A$) by current-voltage converter 42. In most cases, converter 42 may be an operational amplifier with feedback ($Z_F$) and load ($Z_L$) impedances, such that the voltage ($V_A$) generated at the output of the PMT is related to the anode current by:

$$V_A = I_A * (Z_F/Z_L) \quad \text{EQ. 2}$$

Unlike conventional PMT circuits, circuit 30 includes additional circuit elements for measuring an intermediate dynode voltage ($V_D$), in addition to the anode voltage ($V_A$). In one example, the intermediate dynode voltage may be obtained by supplying the photoelectric current ($I_D$) generated at one of the dynode stages 36 to an additional impedance element ($Z_D$), such that:

$$V_D = I_D * (Z_D) \quad \text{EQ. 3}$$

In most cases, the intermediate dynode voltage will be less than the anode voltage, since the dynode voltage represents the photoelectric current before the current is fully amplified at the anode. As described in more detail below, the intermediate dynode voltage may be used in place of the anode voltage for detecting defects on a specimen. For example, the intermediate dynode voltage may be used for detecting defects once the photoelectric current at the anode causes the anode to saturate. Switching logic 44 is included within circuit 30 for monitoring the anode voltage and switching to the intermediate dynode voltage once the anode current reaches saturation.

The level at which anode 38 becomes saturated may depend on several factors including, but not limited to, the material composition and geometrical structure of the anode, the high voltage between the last dynode and the anode, and the configuration of the voltage-divider chain. As known in the art, an element may become "saturated" when any further change in input no longer results in an appreciable change in the output signal generated by that element. In some cases, anode 38 may provide a highly linear anode current up to about 10 mA. The anode may then become saturated if the amount of light entering the PMT causes the anode current to rise above approximately 10 mA. It is noted, however, that smaller or larger saturation levels may be appropriate in other embodiments of the invention. In some cases, for example, larger saturation levels may be appropriate when the anode current remains substantially linear up to about 100 mA.

To avoid anode saturation, switching logic 44 may switch to the intermediate dynode voltage ($V_D$) once the anode current ($I_A$) approaches, reaches or surpasses the saturation level. For example, switching logic 44 may use the anode saturation level, or a value slightly above or slightly below such level, as a predetermined threshold level. During circuit operation, switching logic 44 monitors the anode current ($I_A$) while supplying the anode voltage ($V_A$) to downstream processing components (e.g., ADC 22 and processor 24) as an output signal ($V_{OUT}$) of the detector. When the anode current reaches the predetermined threshold level, switching logic 44 uses the intermediate dynode voltage ($V_D$) as the detector output signal ($V_{OUT}$). Regardless of whether the anode or dynode current is used, the detector output signal forwarded by switching logic 44 may be amplified by ADC 22 by a substantially consistent amount.

Switching logic 44 may be implemented as hardware, software, or a combination of both (i.e., firmware). As such, switching logic 44 may be located within or adjacent to circuit 30 as a combination of logic elements, which perform the functionality embodied within switching logic 44. On the other hand, the functionality may be implemented with program instructions, which may be stored and executed "on-chip" or "off-chip." For example, switching logic 44 may be implemented as a digital signal processing (DSP) chip coupled to circuit 30, or as program instructions executed by processor 24. Other configurations/implementations of switching logic 44 may be possible and within the scope of the invention. For example, switching logic 44 may preferably monitor the anode voltage ($V_A$) instead of the anode current ($I_A$), and thus, may not be coupled for receiving the anode current, as shown in FIG. 2A.

As noted above, the intermediate dynode voltage is obtained from one of the plurality of dynodes 36. The particular dynode selected may generally depend on a desired gain differential between the anode and dynode voltages. For example, each of the dynodes are supplied with a particular bias voltage generated by voltage-divider chain 40 and the negative high-voltage power supply ($V_{S1}$) coupled thereto. The high-voltage power supply may generally be chosen to provide a particular amount of overall (or "tube") gain. In most cases, each of the dynodes 36 may be supplied with a successively less negative potential, due to the increasing series resistance encountered along the voltage-divider chain. When supplied with a negative power supply of about −1000V, for example, the impedance elements (e.g., Z1 to Z9) within voltage divider chain 40 may be configured to supply successively less negative potentials to the dynode chain, such that −900V is supplied to the first dynode, −800V is supplied to the second dynode, and so forth. The potential difference between voltages supplied to a selected dynode and the anode determine the gain differential therebetween.

A desired gain differential, and thus, a desired dynode may be selected based on variations in the light intensity entering the PMT. For high-intensity applications, a dynode near the beginning of the chain may be selected to produce a larger gain differential between the dynode and anode voltages. Such a large gain differential may allow substantially larger amounts of light to be detected after the anode becomes saturated. On the other hand, dynodes further down the chain may be selected to produce smaller gain differentials, which may suffice for measuring a smaller range of light intensities.

In some embodiments, a dynode near the middle of the dynode chain may be selected for producing a medium gain signal. As such, the circuits and methods described herein may provide the user with a range of possible gain differentials.

This range may be approximately equal to about $G^{((n-m)/n)}$, where G is the total PMT Gain (cathode to anode), m is the position of the selected intermediate dynode (counting from the cathode), and n is the total number of dynodes.

In the embodiment of FIG. 2A, the selected dynode is disconnected from the voltage-divider chain, and the intermediate dynode voltage is measured across the additional impedance element ($Z_D$). The additional impedance element may be implemented with substantially any passive or active element, although a simple resistance may be preferred. In general, the size of the additional impedance element should be chosen so that the signal measured there across is substantially equal to the signal level at the anode. As shown in FIG. 2A, an additional power supply ($V_{S2}$) may also be needed for measuring the intermediate dynode voltage. In some cases, the additional power supply level may be set to provide the potential, which would have been supplied to the selected dynode if the dynode had not been disconnected from the voltage-divider chain.

Figure 2B:
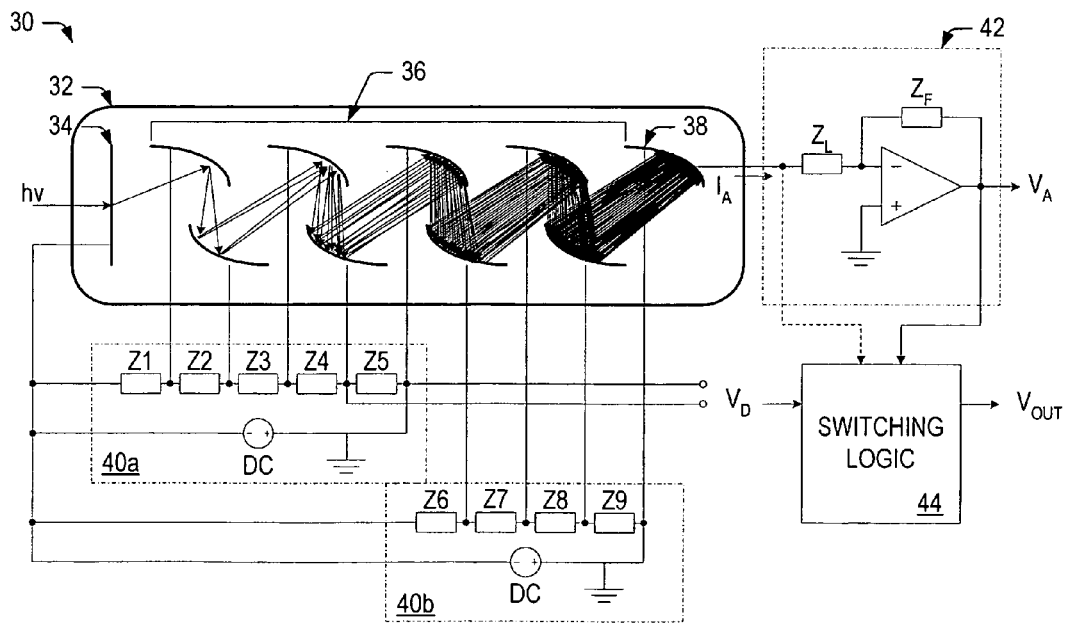
FIG. 2B is a block diagram of an exemplary circuit included within the detection subsystem of FIG. 1 for detecting the light scattered from the specimen, according to a second embodiment of the invention.

FIG. 2B illustrates an alternative embodiment of circuit 30. Similar reference numerals are used to denote similar features between the embodiments shown in FIGS. 2A and 2B; therefore, detailed description of such features will not be repeated for purposes of brevity. Similar to FIG. 2A, the embodiment shown in FIG. 2B includes a PMT detector 32 having a cathode 34, a plurality of dynodes 36 and an anode 38. In some embodiments, the photoelectric current ($I_A$) generated at the anode may be supplied to current-voltage converter 42 and switching logic 44. Once the anode current ($I_A$) reaches a predetermined threshold level (associated with anode saturation), the switching logic may switch to supplying the intermediate dynode voltage ($V_D$) to downstream processing components. In other embodiments, the anode voltage ($V_A$) may be monitored instead of the anode current ($I_A$). In such embodiments, switching logic 44 may not be coupled for receiving the anode current, as shown in FIG. 2B.

The embodiments shown in FIGS. 2A and 2B differ in the manner in which the intermediate dynode voltage is produced. Instead of a single voltage-divider chain 40, the embodiment of FIG. 2B divides the chain into a first portion 40a and a second portion 40b. The first portion 40a is supplied with a first power supply voltage ($V_{S1}$), while the second portion 40b is supplied with a second power supply voltage ($V_{S2}$). In this configuration, the intermediate dynode voltage can be measured across the last impedance element (Z5) in the first portion 40a. The advantage of this configuration is that saturation of the anode and the portion of the voltage-divider chain (e.g., portion 40b) supplying current to the higher dynodes will not affect the portion of the chain (e.g., portion 40a) supplying the lower dynodes.

Figure 2C:
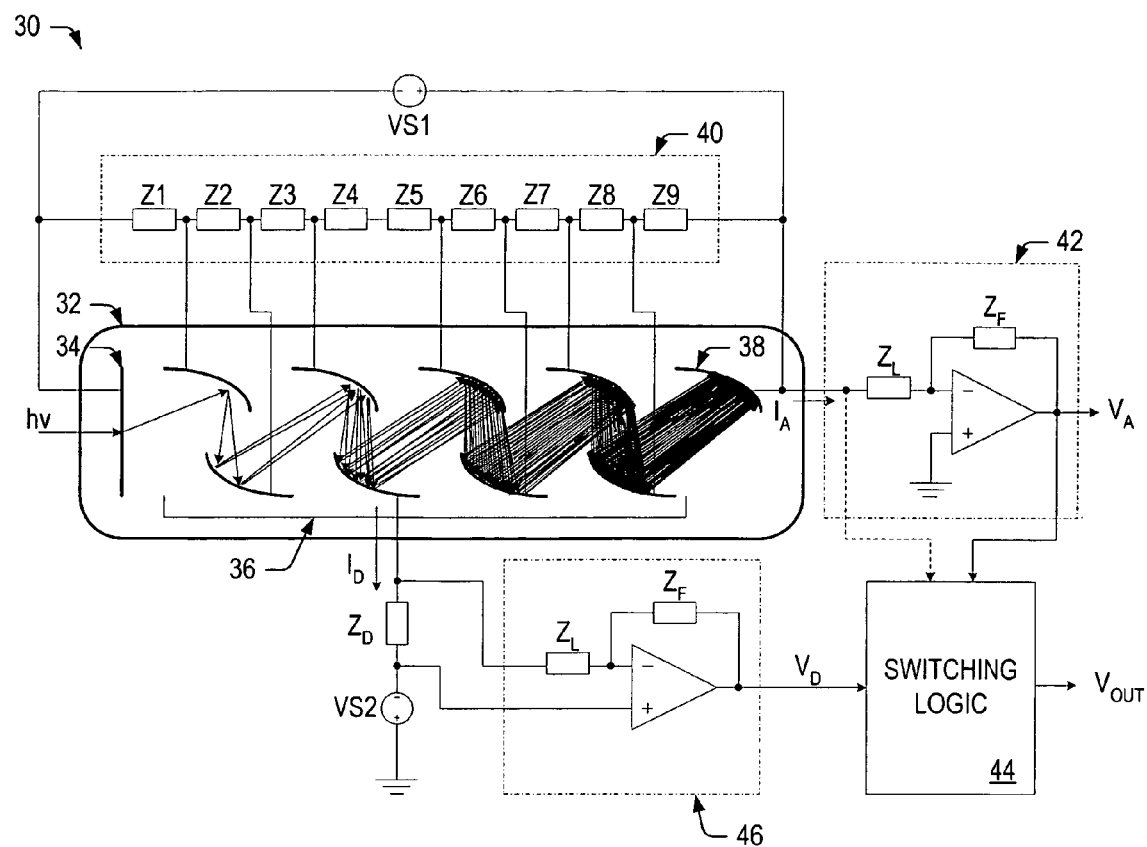
FIG. 2C is a block diagram of an exemplary circuit included within the detection subsystem of FIG. 1 for detecting the light scattered from the specimen, according to a third embodiment of the invention.

FIG. 2C illustrates yet another alternative embodiment of circuit 30. Like before, similar reference numerals are used to denote similar features between the embodiments shown in FIGS. 2A-2C; therefore, detailed description of such features will not be repeated for purposes of brevity. Similar to FIGS. 2A and 2B, the embodiment shown in FIG. 2C includes a PMT detector 32 having a cathode 34, a plurality of dynodes 36 and an anode 38. In some embodiments, the photoelectric current ($I_A$) generated at the anode may be supplied to current-voltage converter 42 and switching logic 44. Once the anode current ($I_A$) reaches a predetermined threshold level (associated with anode saturation), the switching logic may switch to supplying the intermediate dynode voltage ($V_D$) to downstream processing components. In other embodiments, the anode voltage ($V_A$) may be monitored instead of the anode current ($I_A$). In such embodiments, switching logic 44 may not be coupled for receiving the anode current, as shown in FIG. 2C.

FIG. 2C illustrates yet another manner in which the intermediate dynode voltage ($V_D$) may be produced. For example, circuit 30 may include operational amplifier circuit 46 for modifying the gain of the intermediate dynode voltage ($V_D$). The operational amplifier may have a pair of inputs, each coupled to a different terminal of the additional impedance element ($Z_D$). In some cases, load and feedback impedances may be coupled to at least one of the operational amplifier inputs. In this configuration, the intermediate dynode voltage measured across the additional impedance element ($Z_D$) can be modified to produce a signal with somewhat higher or lower gain. For example, the configuration shown in FIG. 2C could be used to bring the intermediate dynode voltage from a high negative potential to a near ground level, which is the same level as the anode output.

Figure 3:
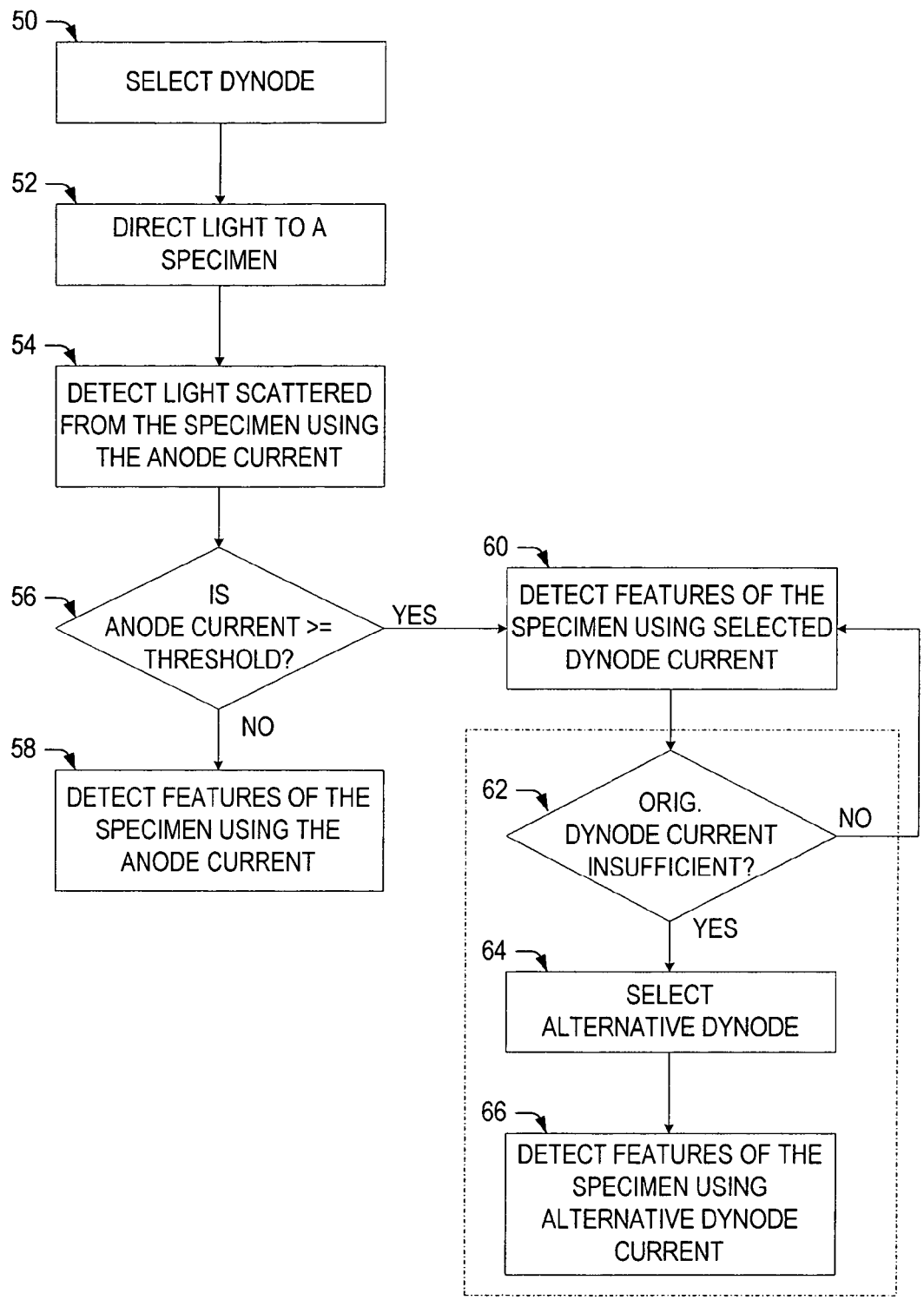
FIG. 3 is a flow chart diagram of an exemplary method for inspecting a specimen, in accordance with the first, second and third embodiments of the invention.

FIG. 3 is a flow chart diagram illustrating an exemplary method for inspecting a specimen using the inspection system of FIG. 1 and the circuits shown in FIGS. 2A and 2B. Various method steps set forth in FIG. 3 may be performed by components included within the inspection system, although certain steps may be performed by a user of the inspection system.

In some embodiments, the method may begin by selecting a dynode (in step 50) to be used for measuring an intermediate dynode voltage. In some cases, a particular dynode may be selected by a user of the inspection system to provide a desired gain differential between the selected dynode and the anode of the PMT. The desired gain differential may be an assumption, an educated guess or a predetermined amount based on expected or previous levels of scattered light intensity. In other cases, the particular dynode may be automatically selected by an inspection system component (e.g., processor 24) based on the expected or previous levels of scattered light intensity.

In step 52, light is directed to a specimen under observation. As noted above, the term "specimen" may refer to a wafer, a reticle or any other sample that may be inspected for defects, features, or other information (e.g., an amount of haze or film properties) known in the art. In the embodiments described herein, the system used for inspecting the specimen is a dark-field optical inspection system, which measures scattered rather than reflected light. Therefore, the method may continue by detecting light scattered from the specimen (in step 54) using the anode current from a photomultiplier tube (PMT). The PMT may be configured as shown in FIG. 2A or 2B. As shown in FIG. 3, the anode current may be used for detecting the scattered light, as long as the anode current remains below a predetermined threshold level. This threshold level may be set manually by a user of the system, or automatically by a system component, based the type/configuration of the PMT. In most cases, the predetermined threshold level may be close or equal to a saturation level associated with the anode.

If the anode current remains below the predetermined threshold (in step 56), features, defects and/or light scattering properties of the specimen may be detected using the anode current (in step 58). Otherwise, the current from the selected dynode may be used for such detecting (in step 60). Using the dynode current may allow significantly larger amounts of scattered light to be measured at the dynode than can be measured at the anode. This is due to there being less amplification at the dynode, which may enable approximately 1 to 1000 times larger signals to be measured at the dynode (using, e.g. a middle dynode) without dynode saturation. To maintain accuracy, however, the dynode current must be multiplied by a calibration ratio approximately equal to the gain ratio of the anode and intermediate dynode. In reference to FIG. 1, the calibration ratio may be applied to the dynode current by system processor 24 or another system component (e.g., an analog or data processing board). Regardless of how the calibration ratio is applied, use of the calibration ratio enables the dynode current to be used for detecting defects, as if it had been generated at the anode.

In some cases, the method may end at step 60. In other cases, however, the method may include additional steps (e.g., steps 62, 64 and 66) if the dynode originally selected (in step 50) is for some reason insufficient for current or subsequent measurement purposes. For example, a relatively low gain dynode may be insufficient for detecting extremely low-light signals. On the other hand, a relatively high gain dynode may saturate when extremely high intensity light is supplied to the PMT. If the originally selected dynode is determined to be insufficient (in opt. step 62), an alternative dynode may be selected (in opt. step 64) and used for detecting the features, defects and other light scattering properties of the specimen (in opt. step 66). The alternative dynode may be selected by a user or component of the inspection system during the measurement operation currently underway, or in preparation for a next measurement operation to be performed.

FIGS. 1-3 illustrate exemplary inspection systems, circuits and methods for improving defect detection by increasing the measurement detection range of a PMT detector, while maintaining detection signal linearity and stability. For example, the anode current may be used for detecting scattered light on the low-intensity side, whereas the intermediate dynode current may be used for detecting on the high-intensity side. Unlike conventional PMT detectors, which have limited detection range due to the inevitable anode saturation, the PMT detector described herein extends the measurement detection range (on-the-high-intensity side) by switching to lower gain dynode currents once the anode becomes saturated. In this manner, the PMT detector described herein may be used to detect substantially more features, defects or light scattering properties of the specimen by dynamically switching between a higher sensitivity, lower saturation detection signal (obtained from the anode current) and a lower sensitivity, higher saturation detection signal (obtained from the dynode current). The anode current may be used for detecting features, such as small defects with low scattering intensity, whereas large, highly scattering defects may be detectable with the dynode current.

In addition to extended detection range, the PMT detector described herein maintains detection signal linearity and stability by avoiding anode saturation with a simple, yet highly-effective solution. In addition, the PMT detector of the present invention avoids the elaborate calibrations and complex circuitry often required in prior art designs to compensate for non-linear and transient effects, which may be introduced when attempting to change the PMT gain "on-the-fly." Furthermore, the present invention provides these advantages while using a single detector, and thus, avoids the additional optics and control circuitry required when using multiple detectors to extend the measurement detection range. As such, the present invention may provide significant savings in both space consumption and cost.

Figure 4A:
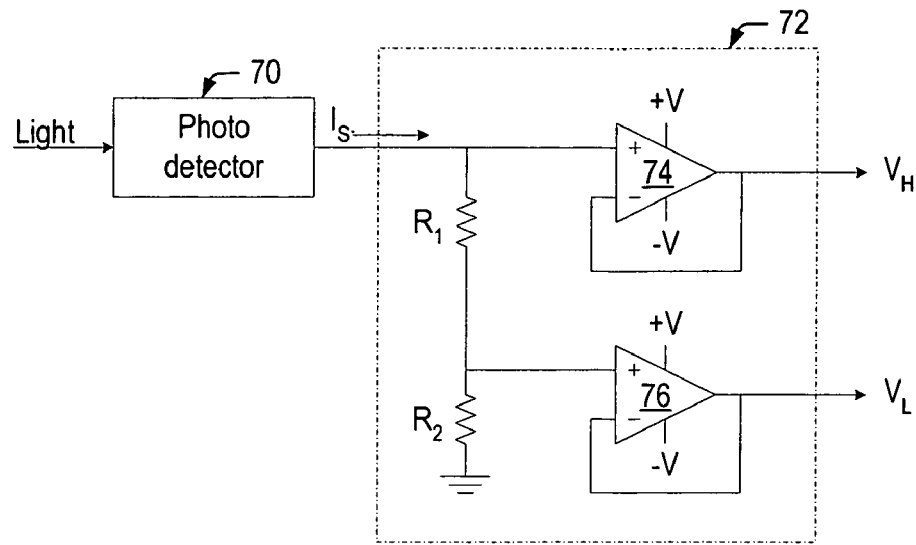
FIG. 4A is a block diagram of an exemplary circuit included within the detection subsystem of FIG. 1 for detecting the light scattered from the specimen, according to a fourth embodiment of the invention.
Figure 4B:
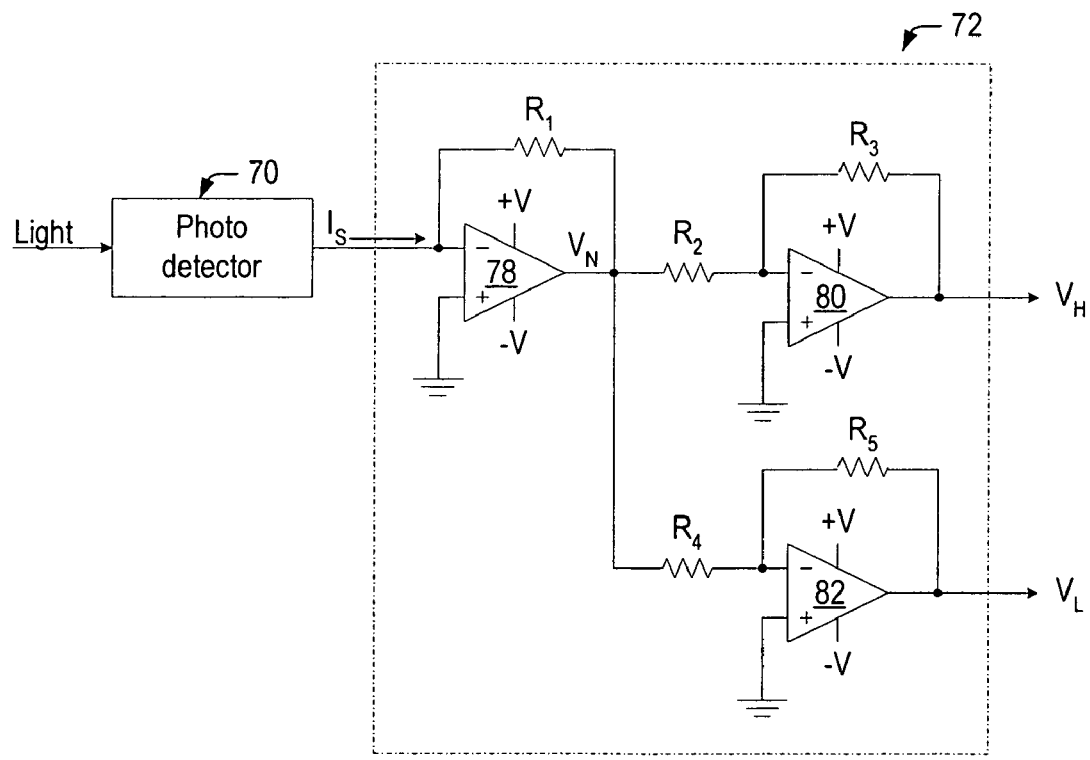
FIG. 4B is a block diagram of an exemplary circuit included within the detection subsystem of FIG. 1 for detecting the light scattered from the specimen, according to a fifth embodiment of the invention.
Figure 5:
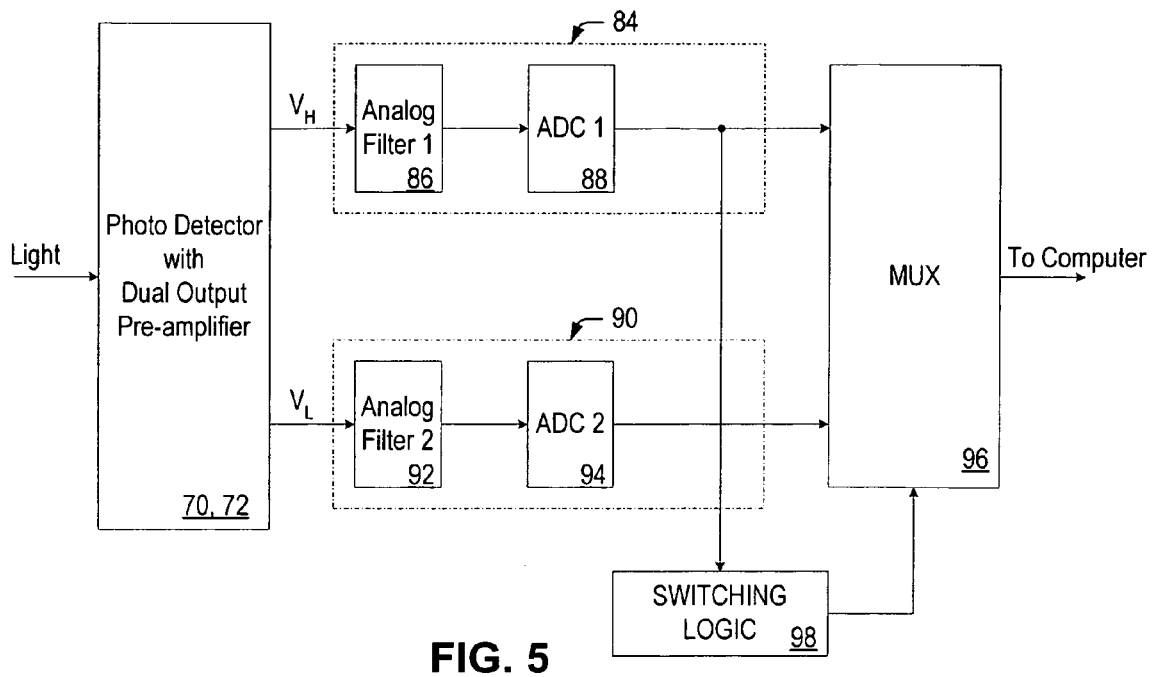
FIG. 5 is a block diagram of exemplary electronics that may be used for filtering, digitizing and switching between the signals generated by the circuits of FIGS. 4A and 4B.
Figure 6:
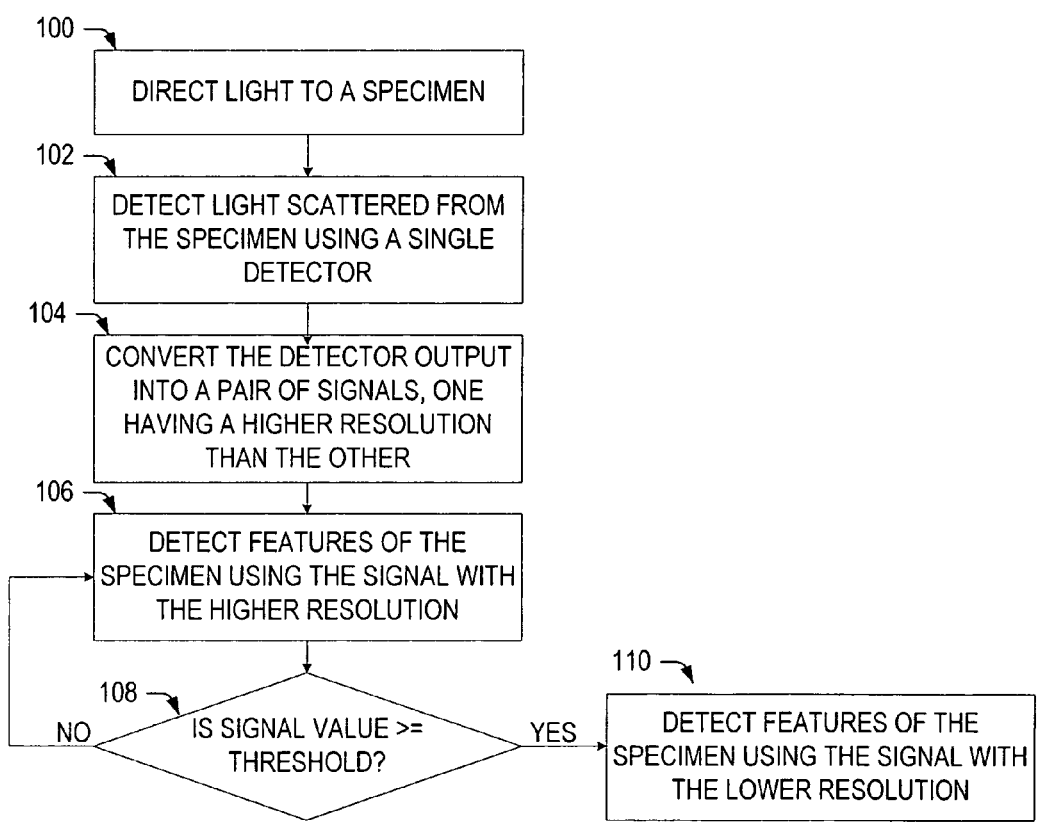
FIG. 6 is a flow chart diagram of an exemplary method for inspecting a specimen, in accordance with the fourth and fifth embodiments of the invention.

FIGS. 4-6 illustrate exemplary circuits, systems and methods for overcoming the detection range limitations typically set by amplifier saturation and the fixed bit range of analog-to-digital converters (ADC). Though relatively few embodiments are shown, one skilled in the art will readily understand how the various concepts described herein could be applied to produce alternative embodiments with similar functionality.

FIGS. 4A and 4B illustrate exemplary embodiments of detector and amplifier circuitry that may be used within an inspection system for detecting light scattered from a specimen. The detector circuitry 70 shown in FIGS. 4A and 4B includes only one photodetector for detecting the light scattered from the specimen and for converting the light into an electrical signal. As noted above, a "single detector" may have only one sensing area or several sensing areas embodied within a single enclosure. Therefore, the detectors shown in FIGS. 4A and 4B may include a single detector with only one sensing area, or a single detector array with multiple sensing areas. In general, detector circuitry 70 may include substantially any technology which is suitable for detecting light scattered from a specimen. Exemplary detectors include, but are not limited to, a photodiode, a phototube, a photomultiplier tube (PMT), a time delay integration (TDI) camera and a charge-coupled device (CCD) camera.

Amplifier circuitry 72 is generally configured for producing of a pair of output signals in response to the electrical signal generated by detector circuitry 70. For this reason, amplifier circuitry 72 may be referred to herein as a "dual-output amplifier." In the embodiments shown, amplifier circuitry 72 is configured for generating a high resolution (high gain) output signal and a low resolution (low gain) output signal from the electrical signal. As described in more detail below, the high resolution signal can be used for detecting features, defects and/or light scattering properties of a specimen when the scattered light falls within a low-intensity range. If the high resolution signal becomes saturated, the low resolution signal can be used for detecting additional features or properties of the specimen that tend to scatter more strongly (i.e., when the scattered light falls within a high-intensity range). Means are provided below (e.g., in FIGS. 5-6) for dynamically switching between the high resolution and low resolution signals during an inspection system scan of a specimen, thereby extending the detection range of the inspection system by overcoming the limitations typically set by conventional amplifier and ADC circuitry.

A first embodiment of a dual-output amplifier 72 is shown in FIG. 4A as including a pair of operational amplifiers (74, 76) and a voltage divider network implemented, e.g., with resistors $R_1$ and $R_2$. Operational amplifiers (or "op amps") 74 and 76 are configured as voltage followers with negative feedback. The positive terminals (+) of operational amplifiers 74 and 76 are coupled for receiving the photodetector current ($I_S$) generated by detector 70 multiplied by some resistive value. In the embodiment of FIG. 4A, the photodetector current is multiplied by the value of resistor $R_2$ for op amp 76, and the value of resistors $R_1$ and $R_2$ for op amp 74. Because of the voltage follower configuration, the voltages present at the output terminals of the op amps is substantially equal to those supplied to their positive terminals. In this configuration, dual-output amplifier 72 may generate a high resolution output signal ($V_H$) and a low resolution output ($V_L$) signal substantially equal to:

$$V_H = V_1 = I_S * (R_1 + R_2) \text{ and} \qquad \text{EQ. 4}$$

$$V_L = V_2 = I_S * R_2. \qquad \text{EQ. 5}$$

The values for resistors $R_1$ and $R_2$ are selected to provide the output signals with substantially different gains. In some cases, for example, the value for resistor $R_1$ may be 15 times larger than that of resistor $R_2$ to generate a high resolution output signal ($V_H$) with 16 times more gain than the low resolution output signal ($V_L$). In one embodiment, resistor $R_1$ may have a value of about 7.5 kΩ and resistor $R_2$ may have a value of about 500Ω.

In the example provided above, the values of $R_1$ and $R_2$ are selected to increase the gain differential (and thus, the detection range of the circuit) by a factor of about 2 to about 16. Other values may be selected to produce the same amount of gain, or to provide more or less gain, in other embodiments of the invention. For example, the resistor values may be selected so as to increase the gain differential (and thus, the detection range of the circuit) from about 2 to about 1024 times the initial range provided by the photodetector alone. The amount by which the detection range can be extended generally depends on the resolution of the downstream analog-digital converter (e.g., ADC 22, FIG. 1) and the desired resolution at the switching point between the high resolution and low resolution signals. For example, the gain differential could be extended by a factor of about 1024 with a 14 bit converter (16383 ADC max) and a desired overlap resolution of 16 ADC.

Another embodiment of a dual-output amplifier 72 is shown in FIG. 4B. In this embodiment, amplifier 72 includes at least three operational amplifiers (78, 80, 82). The first operational amplifier (78) is coupled for receiving the photodetector current ($I_S$) at a negative terminal (−) and a ground potential at a positive terminal (+) of the op amp. Resistor $R_1$ is placed in the negative feedback of op amp 78 for generating an output voltage substantially equal to:

$$V_N = -I_S * R_1 \quad \text{EQ. 6}$$

The second and third operational amplifiers (80, 82) are coupled for generating a pair of output signals based on the nodal voltage ($V_N$) provided by op amp 78. For example, resistors $R_2$ and $R_3$ may be included within op amp 80 for generating a high resolution output signal ($V_H$) substantially equal to:

$$V_H = -V_N[R_3/R_2] \quad \text{EQ. 7}$$

Likewise, resistors $R_4$ and $R_5$ may be included within op amp 82 for generating a low resolution output signal ($V_L$) substantially equal to:

$$V_L = -V_N[R_5/R_4] \quad \text{EQ. 8}$$

As in the above embodiment, the values for resistors $R_1$, $R_2$, $R_3$, $R_4$, and $R_5$ may be selected to provide the output signals with substantially different gains. In one embodiment, the values for resistors $R_3$ and $R_5$ may be set equal to one another, such that EQ. 8 becomes:

$$V_L = -V_N[R_3/R_4] \quad \text{EQ. 9}$$

Now, the values for resistors $R_2$ and $R_4$ may be selected to provide a desired gain differential. In one embodiment, the value for resistor $R_2$ may be 16 times less than that of resistor $R_4$ to generate a high resolution output signal ($V_H$) with 16 times more gain than the low resolution output signal ($V_L$). For example, resistor $R_2$ may have a value of about 62.5Ω, resistors $R_1$ and $R_4$ (which may be equal in some embodiments) may have a value of about 1 kΩ, and resistors $R_3$ and $R_5$ may have a value of about 500Ω. Other values may be selected to produce the same amount of gain, or to provide more or less gain, in other embodiments of the invention. For example, the resistor values may be selected so as to increase the gain differential (and thus, the detection range of the circuit) from about 2 to about 1024 times the initial range provided by the photodetector alone. In some embodiments, one or more additional amplifier circuits may be coupled in series with op amps 80 and 82 to increase/decrease the gain differential of the high resolution and low resolution output signals.

The high resolution and low resolution output signals generated by dual-output amplifier 72 (as shown, e.g., in FIG. 4A or FIG. 4B) are supplied to separate processing channels (84, 90) where they are filtered and converted into a pair of digital signals. As shown in FIG. 5, for example, the high resolution signal ($V_H$) generated by dual-output amplifier 72 may be supplied to processing channel 84 where it is filtered by analog filter 86 and digitized by analog-to-digital converter (ADC 1) 88. Likewise, the low resolution signal ($V_L$) generated by dual-output amplifier 72 may be supplied to processing channel 90 where it is filtered by analog filter 92 and digitized by analog-to-digital converter (ADC 2) 94. Analog filters 86 and 92 may be an anti-aliasing filter such as a Butterworth filter, a Bessel filter, and so on. Substantially any N-bit analog-to-digital converter (88, 94) may be used for converting the high resolution and low resolution analog signals into corresponding digital signals. The gain differential between the analog signals causes the high resolution digital signal to be somewhat larger in value than the low resolution digital signal.

At least one of the digital signals may be supplied to a downstream inspection system component (such as processor 24 of FIG. 1) for further processing. For example, and as shown in FIG. 5, multiplexor 96 may be coupled for selecting either the high resolution digital signal from processing channel 84, or the low resolution digital signal from processing channel 90. The selection is controlled by switching logic 98 which, in most cases, may be coupled to processing channel 84 for monitoring the high resolution digital signal.

As noted above, each of the ADCs may be capable of handling up to N-number of digital bits. In some cases, switching logic 98 may select the high resolution signal for output as long as its digital value remains below a predetermined threshold value associated with the N-bit ADCs (e.g., $2^8 = 256$ for an 8-bit ADC). Once the high resolution signal reaches the predetermined threshold value, switching logic 98 may select the low resolution signal for output. In this configuration, the inspection system may detect features, defects or light scattering properties of the specimen using the larger (i.e., high resolution) digital signal for detecting "low-scattering" features (such as, e.g., small particles or surface defects). Once the predetermined threshold value is reached, the smaller (i.e., low resolution) digital signal may be used for detecting features that tend to scatter more strongly (such as, e.g., large particles or surface defects). A minimum resolution is maintained at the "switch point" between the high resolution and low resolution signals by selecting a "predetermined threshold value," which is less than the max ADC output ($2^N$). For example, a maximum threshold value substantially less than or equal to $2^{N-1}$ may be selected to maintain sufficient resolution at the switch point.

As shown in FIG. 5, switching logic 98 may be implemented as a combination of logic and/or storage elements which, when combined, perform the functionality embodied within switching logic 98. In other embodiments, the functionality may be implemented with program instructions, which may be stored and executed "on-chip" or "off-chip." For example, switching logic 98 may be implemented as a digital signal processing (DSP) chip coupled to processing channels 84 and 90, or as one or more program instructions executed by processor 24. In the latter case, each of the digital signals may instead be supplied to processor 24 and multiplexor 96 may be removed from the block diagram of FIG. 5. Signal selection may then take place via program execution within processor 24. Other configurations/implementations of switching logic 98 may be possible and within the scope of the invention.

FIG. 6 is a flow chart diagram illustrating an exemplary method for inspecting a specimen using the inspection system of FIG. 1 and the circuits and systems shown in FIGS. 4 and 5. Various method steps set forth in FIG. 6 may be performed by components included within the inspection system, although certain steps may be performed by a user of the inspection system.

In some embodiments, the method may begin by directing light to a specimen under observation (in step 100). As noted above, the term "specimen" may refer to a wafer, a reticle or any other sample that may be inspected for defects, features, or other information (e.g., an amount of haze or film properties) known in the art. In the embodiments described herein, the system used for inspecting the specimen is a dark-field optical inspection system, which measures scattered rather than reflected light. Therefore, the method may continue by detecting light scattered from the specimen (in step 102). Unlike some prior art inspection systems, which attempt to extend the detection range by using multiple detectors, the systems and methods described herein use only one detector for such detecting. The single detector used herein may include substantially any photodetector commonly used for detecting scattered light and for converting the light into an electrical signal.

In step 104, the electrical signal generated by the detector is converted into a pair of disproportionately amplified signals. For example, a dual-output amplifier similar to those shown in FIGS. 4A-4B may be used for generating a first signal and a second signal in response to the electrical signal. In some cases, the first signal may have a higher resolution (higher gain) than the second signal for detecting substantially lower levels of scattered light. On the other hand, the second signal may have a lower resolution (lower gain) than the first signal for detecting substantially higher levels of scattered light. In this manner, the lower levels of light detected by the first signal may fall within a first detection range, whereas the higher levels of light detected by the second signal fall within a second detection range. To maintain sufficient resolution at the "switch point," the second detection range may at least partially overlap the first detection range. As noted above, this may be achieved by selecting a predetermined threshold value that is less than a maximum value (e.g., $2^N$) associated with the N-bit analog-to-digital converters 88, 90. In some cases, ADCs 88 and 90 may each have a different number of bits, such as N and M, where one is larger than the other. In such a case, sufficient resolution can still be maintained at the switch point by selecting threshold values, which are less than the maximum values (e.g., $2^N$ and $2^M$) associated with N-bit ADC 88 and M-bit ADC 90.

In most cases, the first (high resolution) signal may be used for detecting features, defects or light scattering properties of the specimen until the first signal reaches the predetermined threshold value (in step 106). However, once the first signal reaches the predetermined threshold value (in step 108), the second (low resolution) signal may be used for detecting the features, defects or light scattering properties of the specimen (in step 110). For example, while the first signal is being used for detecting, switching logic 98 may compare a digital value of the first signal to the predetermined threshold value. Switching logic 98 may subsequently switch to the second signal once the digital value of the first signal reaches and/or surpasses the predetermined threshold value.

FIGS. 4-6 illustrate exemplary inspection systems, circuits and methods for improving defect detection by increasing the measurement detection range of the amplifier and analog-digital circuitry included within an inspection system. For example, a dual-output amplifier may be used for generating high resolution and low resolution output signals from the electrical signal provided by a single photodetector. The systems, circuits and methods described herein avoid saturating the amplifier and analog-digital circuitry by dynamically switching between the high resolution and low resolution output signals during an inspection scan. This essentially increases the measurement detection range and enables more features, defects or light scattering properties of the specimen to be detected by extending the range of defect sizes that can be detected with the two output signals. In one example, the high resolution signal may be used for detecting defects in the range of about 40 nm to about 155 nm, while the low resolution signal may be used for detecting defects in the range of about 80 nm to about 500 nm. Other embodiments may be capable of detecting somewhat smaller or larger defects. Factors that determine the size of defects that can be detected with the present system and method include, but are not limited to, laser power, wavelength, surface topology, spot-size, polarization, collection angles, detector efficiency, and noise. Overlapping the detection ranges ensures that there will be sufficient resolution at the "switch point" between the high and low resolution signals.

The systems, circuits and methods described herein also avoid the additional space consumption and costs associated with conventional inspection systems, which attempt to extend measurement detection range by using expensive optics to split the scattered light amongst multiple detectors. By using only one photodetector, the present invention may also improve the sensitivity of the detected signal by avoiding the signal-to-noise drop that would occur if the scattered light were split amongst multiple detectors.

In addition to the embodiments shown in FIGS. 4-6, the concepts described herein could be extended to more than two amplifier outputs. For example, the amplifier designs shown in FIGS. 4A and 4B could be modified to generate three or more output signals (e.g., a high resolution, medium resolution and low resolution signal) from the electrical signal produced by detector 70. If a PMT detector similar to those shown in FIGS. 2A and 2B is used to implement detector 70, the system shown in FIG. 5 could also be modified to switch to an intermediate dynode voltage if, e.g., the low resolution signal becomes saturated. Other configurations and/or implementations may be possible and, thus, are considered within the scope of the invention.

Figure 7:
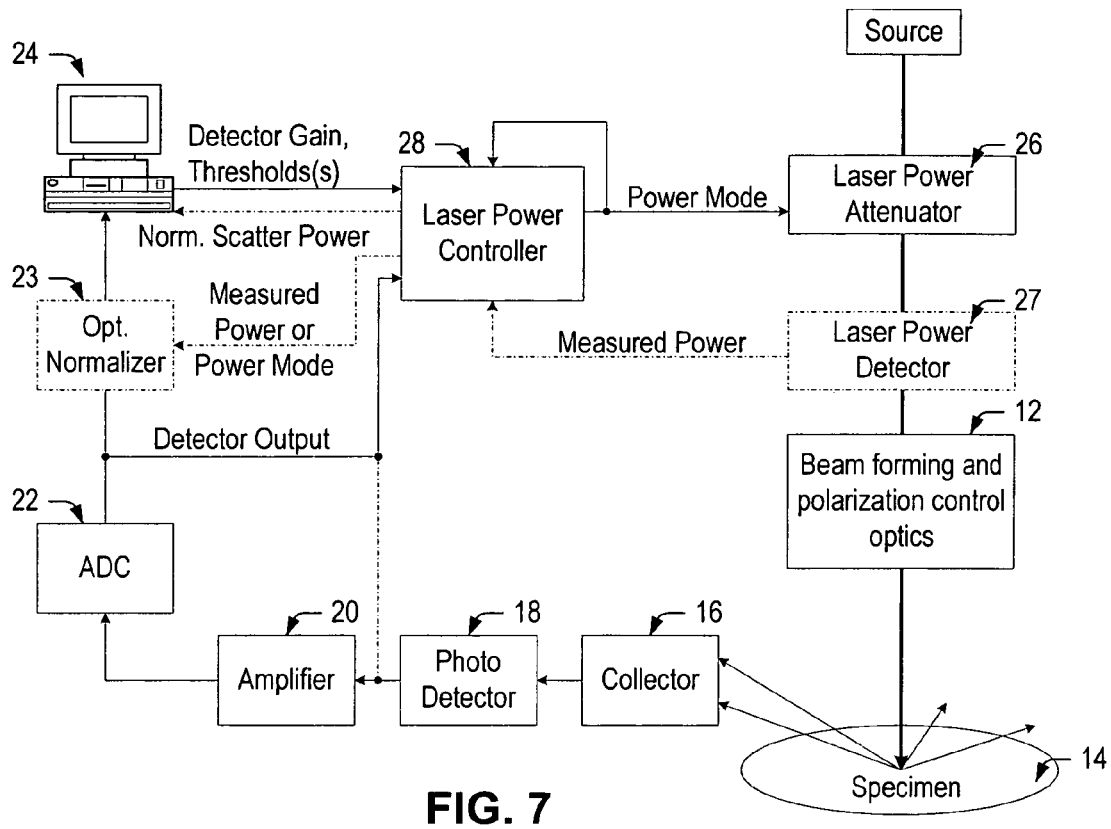
FIG. 7 is a block diagram of another exemplary inspection system including means for controlling the amount of incident laser power supplied to a specimen under observation.

FIG. 7 illustrates another example of an inspection system that can be used to perform a method for inspecting a specimen, as described herein. In particular, FIG. 7 illustrates one example of an inspection system that may be used to reduce and/or prevent thermal damage to a specimen during a surface inspection scan. Thermal damage is commonly seen in prior art systems when the incident laser light directed to the specimen is absorbed and inadequately dissipated by a feature on the specimen (such as large particles or defects). In addition to preventing thermal damage, the inspection system of FIG. 7 can be used to provide yet another means for extending the measurement detection range of an inspection system.

FIGS. 7-12 illustrate exemplary circuits, systems and methods for reducing particle damage during surface inspection scans, which use high-power laser-based inspection systems, by dynamically reducing the incident laser power before scanning over large, highly scattering particles. Though relatively few embodiments are shown, one skilled in the art will readily understand how the various concepts described herein could be applied to produce alternative embodiments with similar functionality.

In high-power laser-based inspection systems, the power density of the incident laser beam typically ranges between about 1 kW/cm$^2$ to about 1000 kW/cm$^2$. Unfortunately, particle damage often occurs during surface inspection scans with high power density laser beams, due to the rapid power transfer from the laser beam to a particle (or a portion of a particle) on the specimen. Particles not capable of dissipating large amounts of power tend to warm up quickly, and often explode due to insufficient power dissipation. For example, organic materials (such as photoresist particles) tend to dissipate significantly less power than inorganic materials (such as metallic particles), and therefore, tend to experience more damage. Unfortunately, exploded particles lead to debris, which can spread a large area of contamination over the specimen.

Methods that may be used to reduce thermal damage include methods for scanning the entire wafer at a reduced laser power (e.g., a factor of 10 less power) or an increased spot size (e.g., 2.5× to 5.7× larger spot size) than the power or spot size known to inflict damage. Another method may exclude the wafer center from inspection by blocking a portion of the incident laser beam. This method reduces thermal damage by eliminating the high power level typically supplied to the center region of the wafer. However, these methods either reduce sensitivity by reducing the signal-to-noise ratio (i.e., when reducing the laser power or increasing the spot size), or result in incomplete inspection of the wafer (i.e., when excluding the center). As such, the above-mentioned methods often miss defects on the wafer, due to poor sensitivity or outright exclusion.

On the contrary, the inventive concepts described herein are based on the observation that larger particles (typically>5 μm) are more likely to be damaged by the incident laser beam than smaller particles. For example, larger particles have more surface area, and as such, tend to absorb significantly more power than smaller particles having less surface area. Larger particles also tend to scatter significantly more light than smaller particles, due to larger surface area and/or increased surface irregularities. For example, the amount of light scattered from a particle of radius, R, is relatively proportional to the particle radius raised to the sixth power (i.e., $R^6$).

The inventive concepts described herein exploit the highly scattering properties of large particles to reduce thermal damage during a surface inspection scan. As set forth in more detail below, thermal damage may be avoided by detecting the presence of a large particle and reducing the incident laser beam power before a main portion of the beam reaches the large particle. In one embodiment, the power reduction may be provided by a fast laser power attenuator, which can be engaged to reduce the incident laser power to "safe" levels when scanning over large particles. The laser power attenuator can be disengaged to maintain (or increase) the incident laser power at "full" power when scanning lower-scatter portions of the wafer.

Turning to the drawings, FIG. 7 illustrates an inspection system similar to the system shown in FIG. 1 and described above. Elements common to both FIGS. 1 and 7 are indicated with similar reference numerals, the description of which will not be repeated herein. Unlike the inspection system of FIG. 1, the inspection system shown in FIG. 7 may be specific to high-power optical inspection systems. As such, light source 10 may include any number of light sources with output power densities ranging from about 1 kW/cm$^2$ to about 1000 kW/cm$^2$. Examples of potential high-power, laser-based sources that may be used for light source 10 include, but are not limited to, a diode laser, a solid state laser, a diode pumped solid state (DPSS) laser, and various gas lasers (such as a helium neon laser, an argon laser, etc.). In some cases, light source 10 may be implemented with a high-power, non-laser-based source, such as an Arc lamp, a Mercury high or low pressure lamp, an LED array, a light bulb, etc. The beam of light generated by light source 10 (i.e., the "generated light") is directed to a surface of specimen 14 through beam forming and polarization control optics 12. To eliminate confusion, the light that reaches the surface of the specimen will be referred to herein as the "incident light" or the "incident laser beam." As described in more detail below, the "incident light" may differ from the "generated light" in one or more ways, including polarization, intensity, size and shape of the spot, etc.

In addition to the elements shown in FIG. 1, the inspection system shown in FIG. 7 may include means for dynamically altering the power level of the incident light supplied to the specimen. For example, laser power attenuator 26 may be arranged between light source 10 and optics 12 for dynamically altering the power level of the incident laser beam during a surface inspection scan. In general, laser power attenuator 26 may be implemented with a selectively transmissive optical component, which may be adapted to transmit a portion of the incident light based on a polarization of the incident light. For example, laser power attenuator 26 may include a wave plate (such as a quarter wave plate) and a polarizing beam splitter, in some embodiments. In this configuration, the wave plate may be used to change the polarization of the incoming light, while the beam splitter functions to transmit one or more select polarizations (e.g., linearly polarized light) and reflect all others (e.g., randomly, circularly or elliptically polarized light). By reflecting portions of the light, the wave plate and beam splitter function to reduce the intensity or power level of the light transmitted there through. However, wave plates and similar optical components (such as neutral density filters) cannot be turned on and off like a switch, and instead, must be moved in and out of the beam path to provide two distinct power levels. In some cases, such movement may not be fast enough to provide dynamic power alteration during a surface inspection scan.

Figure 8:
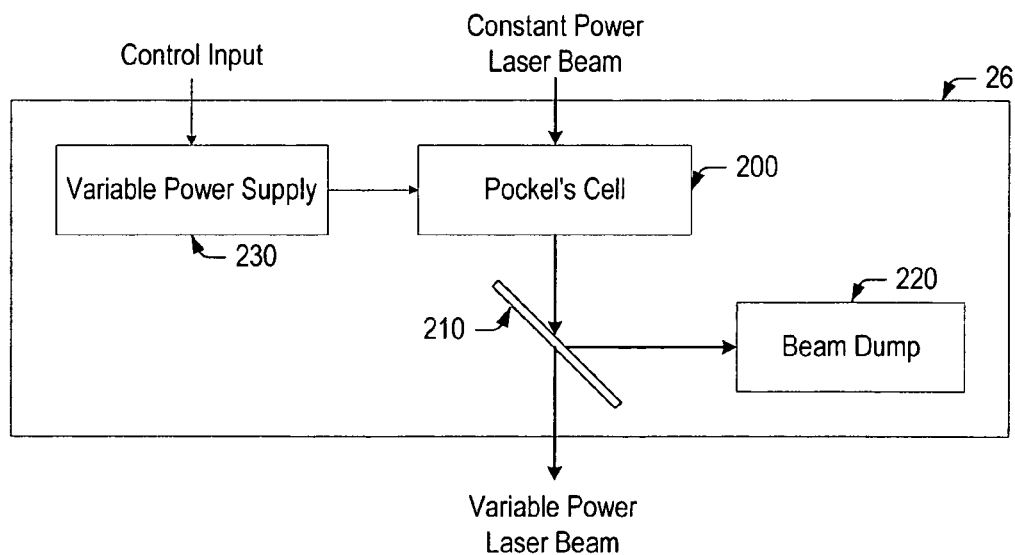
FIG. 8 is a block diagram of an exemplary embodiment of a laser power attenuator, which may be included within the inspection system of FIG. 7.

FIG. 8 illustrates one embodiment of a preferred laser power attenuator 26. In the embodiment shown, extremely fast laser power attenuation is provided by using an electro-optical material 200 to switch between an "on" condition and an "off" condition. When "on," the electro-optical material 200 may change the polarization of the incoming light into a predetermined polarization orientation. This so-called "re-polarized light" may then be supplied to a polarizing beam splitter 210, which may transmit only a portion of the re-polarized light, depending on the particular polarization output from the electro-optical switch. Remaining portions of the re-polarized light may be reflected and absorbed by beam dump 220. In some cases, the electro-optical material may switch between "on" and "off" conditions within a time span of a few nanoseconds to a few microseconds. In this manner, fast laser power attenuation can be provided by using an electro-optical switch, rather than moving a selectively transmissive optical element in and out of the beam path.

In a specific embodiment, laser power attenuator 26 may be implemented with a high-speed electrically-controlled optical shutter, known as a Pockel's Cell. Initially, Pockel's Cell 200 may be set in the "on" condition to allow the light generated by light source 10 to pass freely through laser power attenuator 26. However, when the presence of a large particle is detected, Pockel's Cell 200 may be switched to the "off" condition to change the polarization of the generated light to a different polarization, which can be at least partially filtered out by polarizing beam splitter 210. To switch between the "on" and "off" conditions, an electrical voltage provided by variable power supply 230 may be supplied to Pockel's Cell 200 to change the polarization of the light passed through the electro-optical material (typically, an electro-optical crystal). As shown in FIG. 8, the voltage supplied to the Pockel's Cell may be determined by a control signal input to variable power supply 230.

In one example, the voltage supplied to Pockel's Cell 200 (i.e., causing the cell to switch to the "on" condition) may alter the characteristics of the electro-optical crystal so that it changes linearly polarized light into circularly polarized light, a phenomenon frequently referred to as a "quarter wave phase shift." If the circularly polarized light is supplied to a beam splitter, which is primarily configured for reflecting circularly polarized light, the intensity or power level of the light output from laser power attenuator 26 can be reduced by setting the Pockel's Cell in the "on" condition. On the other hand, the intensity or power level of the light output from laser power attenuator 26 can be maintained (or increased) by setting the Pockel's Cell in the "off" condition.

However, the intensity of the light output from power attenuator 26 is dependent on polarizing beam splitter 210, as well as the phase shift produced by Pockel's cell 200. For example, beam splitters typically discriminate between two orthogonal polarizations such as, e.g., the so-called "S" and "P" polarizations. However, other polarizations of light (such as C-polarized light) may be partially transmitted, and therefore, partially redirected (e.g. into the beam dump) by the beam splitter. If a voltage is applied such that the Pockel's cell creates a ¼ wave phase shift, incoming linearly polarized light (typical laser output) will become circularly polarized and half of that light will pass through the beam splitter, while the other half is redirected. For a ½ wave shift, no light will pass through the beam splitter except for some leakage due to imperfection of the optical components. In other words, virtually all of the incoming light will be redirected when the Pockel's Cell is configured to produce a ½ wave shift (assuming that in the power off state all light passes through the beam splitter).

In some cases, the constant power laser beam generated by light source 10 can be divided into two distinct power levels (e.g., a "safe" power level and a "full" power level) by dynamically switching an electro-optical shutter (such as a Pockels's Cell) between "on" and "off" conditions. The safe power level may be substantially less than the full power level to prevent thermal damage when scanning over large particles. For example, the safe power level may be some percentage (ranging, e.g., between about 1% and about 50%) of the full power level. In one embodiment, the safe power level may be about 10% of the full power level. Other possibilities exist and may generally depend on the incident laser power, as well as the size and material composition of the particles being scanned.

Figure 11:
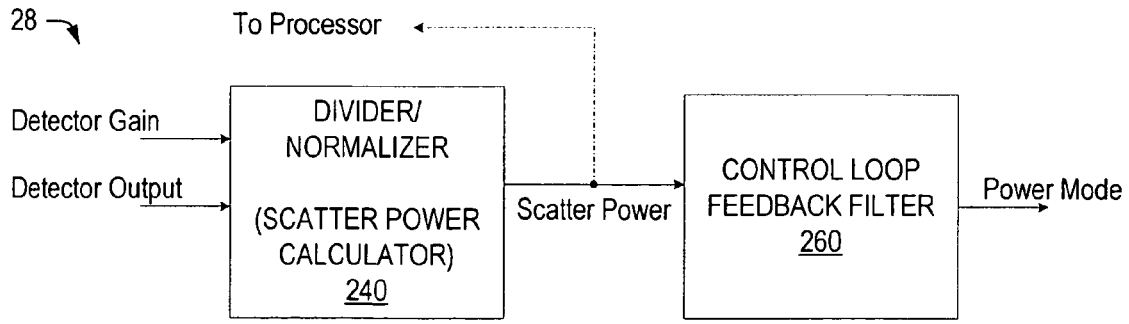
FIG. 11 is a block diagram of yet another exemplary embodiment of a laser power controller, which may be included within the inspection system of FIG. 7.

In other cases, an electro-optical shutter (such as a Pockels's Cell) may be configured for generating more than two distinct power levels. For example, a Pockel's Cell can be driven to produce substantially any phase shift, and thus, may be combined with a polarizing beam splitter to create substantially any output power level. In other words, the embodiment shown in FIG. 8 could be used to create substantially any number of distinct power levels. In some cases, circuitry and/or software may be included to provide a continuous power level adjustment, e.g., in the form of a closed feedback loop, as shown in FIG. 11.

Other means may be used for dynamically altering a power level of the incident light supplied to a specimen, in addition to the examples described above and shown in FIGS. 7 and 8. For example, such means may include, but are not limited to, direct power adjustment of the light source, a fast micro mirror, an acousto-optical deflector (AOD), and a fast mechanical shutter. As such, the present invention may encompass any appropriate means for dynamically altering the power level of a laser beam, given that such means provide a relatively fast response (e.g., on the order of a few nanoseconds to a few microseconds) and at least two distinct power levels (e.g., "safe" and "full" power levels). In general, the response time should be faster than the typical time it takes to damage a particle. Other factors that may influence the choice of a fast laser power attenuator include, but are not limited to, optical transmission, cost, reliability, and life-time.

In addition to the various means described above for dynamically altering a power level of a laser beam, the inspection system of FIG. 7 provides means for controlling such alteration. For example, laser power controller 28 may be coupled between one or more elements of the detector subsystem (e.g., collector 16, photodetector 18, amplifier 20, ADC 22 and processor 24) and laser power attenuator 26. As described in more detail below, laser power controller 28 may continuously monitor the light scattered from specimen 14 and detected by the detector subsystem to determine whether the detected scattered light is above or below a predetermined threshold level. Based on such determination, laser power controller 28 may instruct laser power attenuator 26 to provide the incident light to the specimen at either a first power level (e.g., a "full" power level) or a second power level (e.g., a "safe" power level). The laser power controller may also cause the laser power attenuator to provide, e.g., a third, fourth, or fifth (and so on) power level to the specimen, if more than two power levels are available and circumstances warrant (or benefit from) such levels.

In general, the predetermined threshold level may be set to reduce or prevent thermal damage that may be caused when incident light directed to the specimen is absorbed and inadequately dissipated by a feature on the specimen. The predetermined threshold level is typically based on the incident laser power density, and more specifically, on a power density associated with the onset of thermal damage inflicted on a feature or particle of certain size. For example, the predetermined threshold level may be selected from a group of incident laser power densities ranging from about 1 kW/cm$^2$ to about 1000 kW/cm$^2$ to avoid damaging relatively large particles (e.g., >5 μm). When scanning organic materials, the predetermined threshold level may range from about 1 kW/cm$^2$ to about 100 kW/cm$^2$ to avoid damaging large particles with relatively poor heat dissipation. As shown in FIG. 7, the predetermined threshold level may be supplied from processor (or computer system) 24 to laser power controller 28. The predetermined threshold level may be selected manually by a user of the system, or automatically by processor 24.

If the detected scattered light remains below the predetermined threshold level, laser power controller 28 may instruct laser power attenuator 26 to maintain the power of the incident laser beam at the "full" power level. However, laser power controller 28 may provide instructions to reduce the power of the incident laser beam to a "safe" power level, if the detected scattered light exceeds the predetermined threshold level (indicating, e.g., that a large particle is near). Once the incident laser beam scans over the large particle (or other highly scattering feature), the detected scattered light may fall back below the predetermined threshold level, causing laser power controller 28 to instruct the laser power attenuator to increase the incident laser beam back to "full" power.

In this manner, the inspection system described herein may be uniquely configured for detecting features of relatively small size by directing the incident light to the specimen at a first power level (e.g., "full" power), while features of relatively larger size may be detected by directing the incident light to the specimen at a second power level (e.g., "safe" power). In the current system, the larger features may be detected, without inflicting thermal damage on those features, by setting the second power level substantially lower than the first. If more than two power levels are available, laser power controller 28 may compare the detected scattered light against two or more threshold levels, and instruct the laser power attenuator to maintain, reduce or increase the incident laser beam to an appropriate power level based on such comparison.

Figure 9:
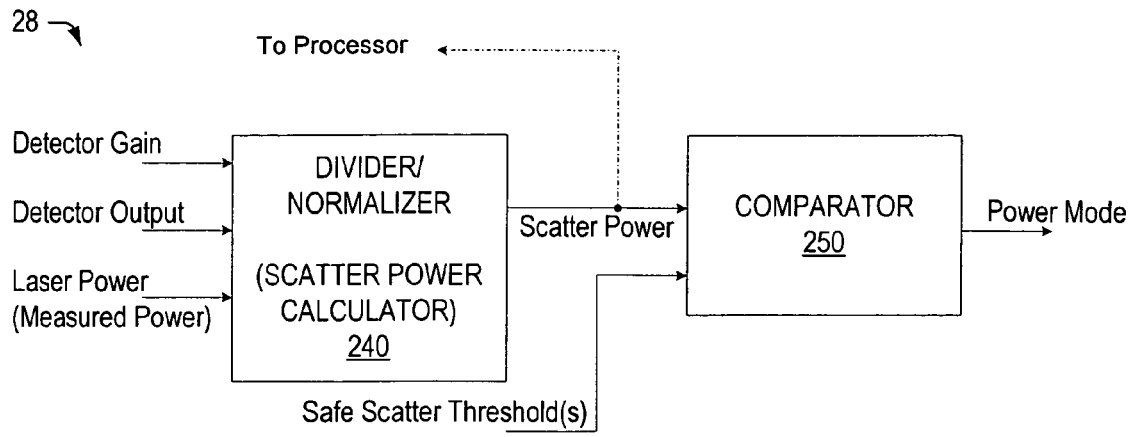
FIG. 9 is a block diagram of an exemplary embodiment of a laser power controller, which may be included within the inspection system of FIG. 7.

FIG. 9 illustrates one embodiment of a preferred laser power controller 28. In the embodiment shown, laser power controller 28 includes divider 240 for normalizing the detector output against the incident laser power and detector gain. As such, divider 240 may be used to calculate the normalized scatter power, and thus, may be alternatively referred to as a scatter power calculator. In one example, the scatter power may be computed by dividing the detector output by the incident laser power and detector gain, or:

$$ScatterPower = \frac{DetectorOutput}{(LaserPower)(DetectorGain)} \qquad \text{EQ. 10}$$

By normalizing the detector output in such a manner, the laser power controller causes the laser power attenuator to consistently switch at the same scatter light level, rather than switching at a given signal level. In other words, all signals become larger when the detector gain is increased. If the detector output is not normalized when the detector gain is increased, switching could occur at a smaller particle size than actually intended. Normalizing the detector output against incident laser power and detector gain enables one to consistently switch (e.g., to a lower power level) once a particle of a given size is detected.

As shown in FIG. 7, divider 240 may receive the detector output (i.e., the scattered light detected from the specimen) as an analog signal from photodetector 18, or alternatively, as a filtered and digitized signal from ADC 22 or processor 24. The detector gain (i.e., the current amplification associated with the detector) is supplied to divider 240 by processor 24, and may be variable or fixed depending on the particular photodetector used. As described in more detail below, however, the incident laser power may be supplied to divider 240 in one of two ways.

In some embodiments, the normalized scatter power signal generated by divider 240 may be fed back to processor 24, as shown by the dotted lines in FIGS. 7 and 9-11. In other words, divider 240 may be used to present the scatter data (i.e., the detector output) as a scan result, which has been normalized against incident laser power and detector gain. By normalizing the data before it is sent to the processor, the actual defect scatter power can be used to accurately detect the size of a defect. For example, if the incident laser power is lowered when scanning over a large particle, the ADC counts (i.e., the detector output) will necessarily be lower than in the unattenuated case. This means that the scan results supplied to the processor will show a smaller defect than what is actually there. Normalizing the scatter data enables the processor to more accurately determine the size of the defect.

In some embodiments, an additional normalizer/divider 23 may be used in the data collection path between ADC 22 and processor 24 for normalizing the scatter power signal against changes in incident laser power. The additional divider 23 may be used along with, or as an alternative to, the normalizer/divider (240) included within laser power controller 28. For example, if two dividers are used, divider 23 may be placed in the data collection path for normalizing the scatter power signal sent to processor 24, while divider 240 is placed in the threshold path for normalizing the scatter power signal sent to another laser power controller component (e.g., comparator 250, as discussed below). However, there may exist other options in which: only one divider is used (either in the data collection path or the threshold path), or no dividers are used (in which case, the system would not support dynamic range extension, as discussed below).

As noted above, the incident laser power may be supplied to divider 240 in one of two ways. In the embodiment of FIG. 9, the actual laser power of the incident beam is measured by laser power detector 27, which may be arranged in the beam path below laser power attenuator 26. In this embodiment, laser power detector 27 is included to monitor the actual intensity or power level output from laser power attenuator 26. The power measured by the laser power detector (i.e., the Measured Power) is supplied to laser power controller 28 for calculating the normalized scatter power. The laser power detector may be implemented with substantially any power detecting means including, but not limited to, a photodiode and a photomultiplier tube (PMT), among others. As described in more detail below, however, laser power detector 27 may not be included in all embodiments of the invention.

As shown in FIG. 9, laser power controller 28 may also include a comparator 250 for comparing the normalized scatter power to one or more predetermined threshold levels supplied by processor 24. As noted above, the threshold level (s) may be selected by a user or processing component of the system to effectively reduce thermal damage when scanning over large (or other highly scattering) particles. In one embodiment, comparator 250 may receive only one threshold level (referred to as a "safe scatter threshold"), which indicates a laser power density associated with a maximum amount of "safe" scatter power. After comparing the normalized scatter power to the safe scatter threshold, comparator 250 may instruct laser power attenuator 26 to maintain, reduce or increase the incident laser beam to an appropriate power level (e.g., a "full" or "safe" power level) by maintaining or changing the Power Mode supplied to the attenuator. In general, the Power Mode may be any control signal that causes the attenuator to maintain or change the output power level. In the embodiment of FIG. 8, for example, the Power Mode supplied to the attenuator may be functionally equivalent to the control signal input to variable power supply 230.

Figure 10:
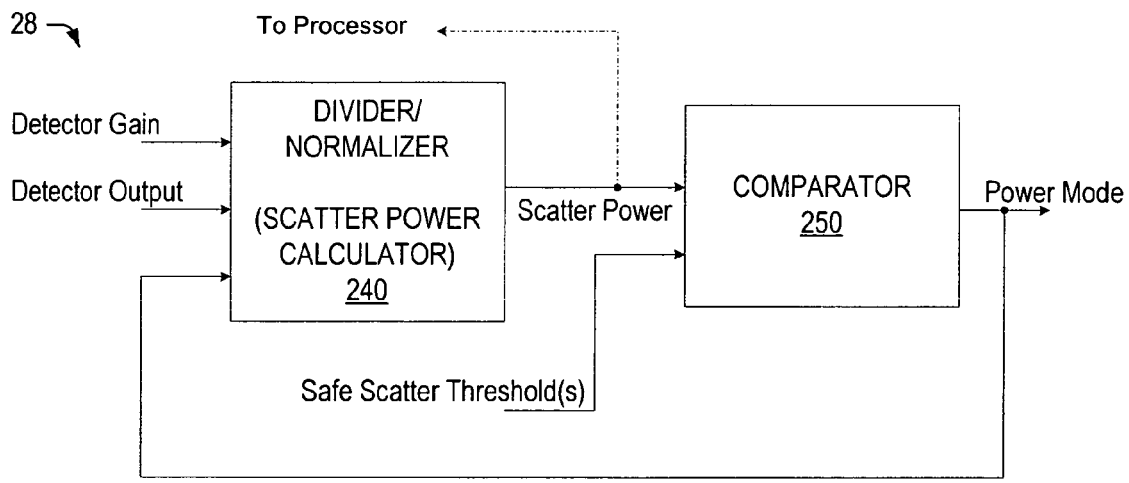
FIG. 10 is a block diagram of another exemplary embodiment of a laser power controller, which may be included within the inspection system of FIG. 7.

FIG. 10 illustrates another embodiment of a preferred laser power controller 28. In particular, FIG. 10 illustrates one manner in which the normalized scatter power can be calculated if a laser power detector is not used to provide a measurement of the actual power level output from laser power attenuator 26. Instead of receiving the Measured Power, divider 240 may be coupled to the output of comparator 250 for receiving the Power Mode control signal supplied to the attenuator. Based on the control signal, divider 240 may determine the appropriate incident laser power to be used in the scatter power calculations by means of, e.g., a look up table. In the embodiments shown in FIGS. 9 and 10, divider 240 and comparator 250 may be implemented with hardware, software or a combination of both. In one example, divider 240 may be implemented in software, whereas comparator 250 may be implemented in hardware.

FIG. 11 illustrates yet another embodiment of a preferred laser power controller 28. In particular, FIG. 11 illustrates one manner in which continuous power adjustment may be provided by laser power controller 28. Like the previous embodiment, divider 240 may be coupled for receiving the detector gain and output signals, and for generating a normalized scatter power signal in response thereto. However, instead of supplying the normalized scatter power signal to a comparator (as shown in FIGS. 9-10), the scatter power signal is supplied to a control loop feedback filter 260, which dynamically adjusts the output Power Mode based on the supplied signal. In FIG. 11, the scatter power signal is used in the feedback loop 260 to adjust the incident laser power, e.g. to achieve a constant detector output signal. Therefore, instead of fixed power levels, the embodiment shown in FIG. 11 provides a continuously adjustable power level.

The circuits and systems shown in FIGS. 7-11 may reduce thermal damage to large particles (e.g., >5 μm) by dynamically adjusting the intensity or power level of the incident laser beam during a surface inspection scan. In one example, thermal damage may be reduced by as much as 100% over fixed incident laser beam inspection systems. The circuits and systems described herein may be tailored to a variety of scan operations by providing one or more preset threshold levels, which may be used for dynamically switching between two or more incident beam power levels during the scan operation. In this manner, thermal damage may be reduced, or even avoided, by reducing the incident laser power to a lower power level (e.g., a "safe" power level) when scanning over large, highly scattering particles. However, detection sensitivity is maintained by scanning lower-scatter regions at a higher power level (e.g., "full" power level), which allows the system to detect smaller defects.

In alternative embodiments of the invention, an adaptive learning process may be used for altering the threshold levels and/or power levels based on previous or current inspection scan results. As one advantage, an adaptive learning process would allow a longer delay time for the switching electronics, because the decision would be made far in advance of the actual switching event, rather than "on the fly" just before switching is needed. Though accuracy may be increased, such an embodiment would obviously increase the complexity (and probably the cost) of the circuits and systems described above. As a mid-range alternative, a scaled relationship between scatter power and incident power levels may be established, in some embodiments, for continuously altering the amount of incident power supplied to the specimen. This alternative could be used to provide a scatter light signal that is always near the optimal range for the PMT, due to the continual adjustment of the incident power supplied to the specimen.

Though the use of a single photodetector is preferred in most embodiments of the invention, an additional detector may be included in some embodiments for selecting an appropriate power level to be supplied to the specimen. If included, the separate detector may be used to monitor the light scattered from the specimen. However, unlike the original detector, which is used for detecting the scattered light so that the incident power level may be adjusted accordingly, the additional detector may be used for selecting a particular threshold level or "switch point", which may then be used for selecting an appropriate power level to be directed to the specimen.

In addition to reducing thermal damage, the circuits and systems shown in FIGS. 7-11 may also be used to increase the measurement detection range of an inspection system. Usually, the detection range of a fixed-power inspection system is limited to the detection range of the photodetector. However, by providing a variable-power inspection system, the present invention significantly increases the measurement detection range by approximately:

$$(\text{Photodetector detection range}) \times (\text{Attenuator detection range}) \qquad \text{EQ. 11}$$

In some cases, the additional detection range provided by the laser power attenuator may increase the overall measurement detection range of the system by about 2 times to 16 times. When combined with other means described herein (such as the improved PMT detector and/or dual-output amplifier), the overall measurement detection range of the inspection system may be improved by about 2 times to 10,000 times over conventional techniques.

Figure 12:
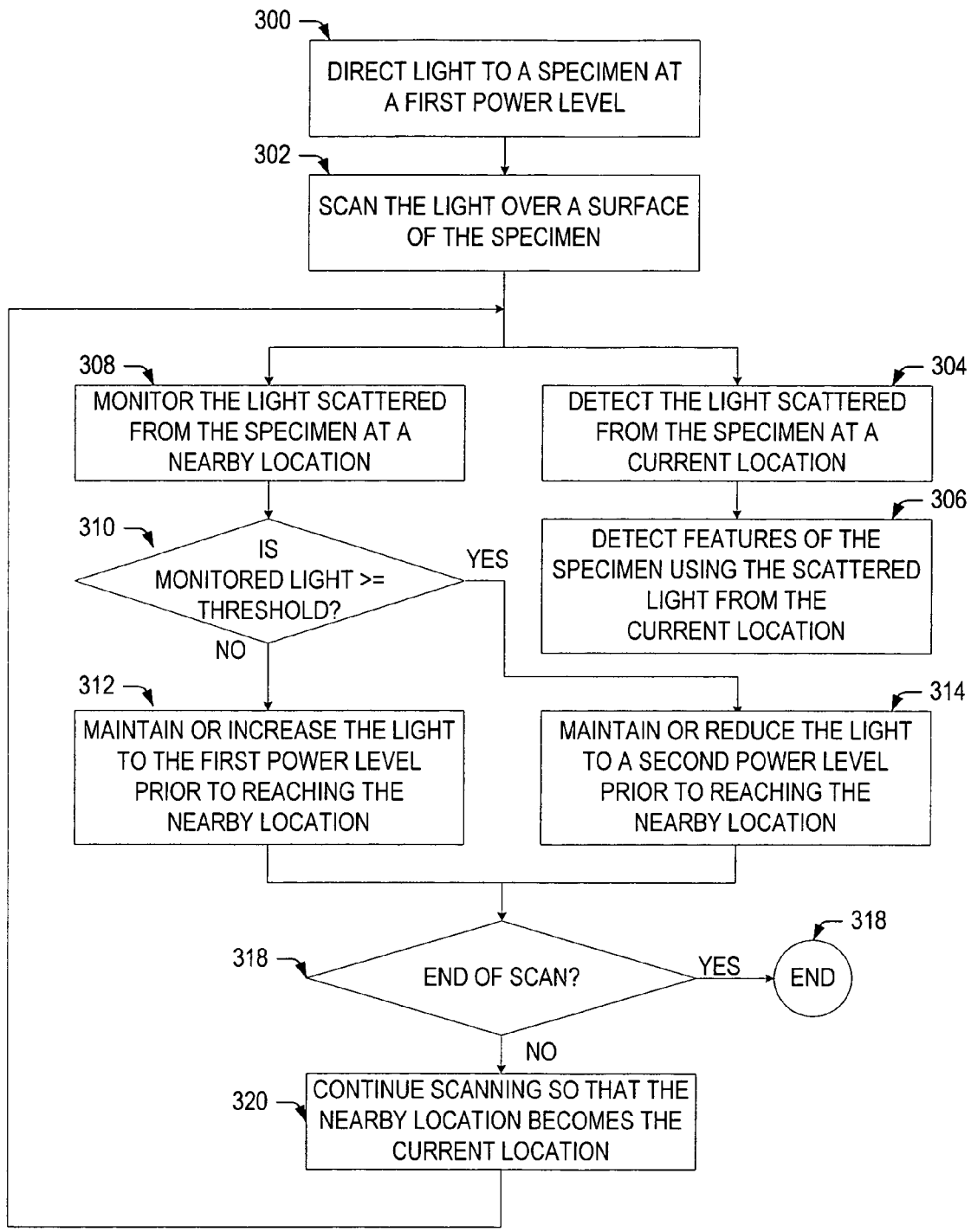
FIG. 12 is a flow chart diagram of a method for dynamically altering the amount of incident laser power supplied to a specimen under observation, so as to reduce thermal damage of large particles and extend the measurement detection range of the inspection system of FIG. 7.

FIG. 12 is a flow chart diagram illustrating an exemplary method for inspecting a specimen with a variable power inspection system, such as the one shown in FIGS. 7-11 and described above. Various method steps set forth in FIG. 12 may be performed by components included within the inspection system, although certain steps may be performed by a user of the inspection system.

In some embodiments, the method may begin by directing light to a specimen at a first power level (in step 300). For example, an incident laser beam may be supplied to the specimen at a relatively high power level (such as a "full" power level) so that relatively small features or defects can be detected. As described in more detail below, the incident laser beam may be subsequently reduced to a lower power level (such as a "safe" power level) so that relatively larger features or defects can be detected without damaging those features. The method shown in FIG. 12 can be modified for dynamically switching between more than two power levels, as desired.

In most cases, the method may detect light scattered from the specimen (in step 304) while scanning the light over a surface of the specimen (in step 302). For example, scattered light may be detected from the specimen when an incident laser beam is directed to a current location on the specimen. The scattered light detected at the current location may be used (in step 306) for detecting features, defects or light scattering properties of the specimen at that location. The beam position may then be scanned to a nearby location, where the process is repeated for detecting features that may be found at the nearby location.

In some embodiments, scanning may be implemented by placing an optical deflector in the beam path leading to the specimen. For example, the deflector may be included within beam forming and polarization control optics 12 of FIGS. 1 and 7. In some embodiments, the deflector may include an acousto-optical deflector (AOD), a mechanical scanning assembly, an electronic scanner, a rotating mirror, a polygon based scanner, a resonant scanner, a piezoelectric scanner, a galvo mirror, or a galvanometer. In some embodiments, the deflector may scan the light beam over the specimen at an approximately constant scanning speed. For example, the light beam may be scanned over the specimen at a constant scanning speed selected from a range of speeds between about 0 m/s and about 24 m/s. In other embodiments, the deflector may scan the light beam over the specimen at a variable scanning speed ranging between about 0 m/s to about 24 m/s. However, a deflector may not be needed to implement scanning in all embodiments of the invention. For example, a normal incidence beam of light may be scanned over the specimen by relative motion of the beam forming optics with respect to the specimen, and/or by relative motion of the specimen with respect to the optics.

During the scanning process, the method monitors light scattered from the specimen at a nearby location (in step 308), while light scattered from the specimen is detected at the current location (in step 304). For example, an incident laser beam may be supplied to the specimen with a power density distribution that peaks near the middle of the distribution and tapers off near the edges of the distribution. As used herein, the middle of the distribution will be referred to as the "main beam," while the edges are referred to as the "beam skirt." One example would be a power density distribution with a main lobe and at least one side lobe on each side of the main lobe; the side lobes having a smaller power density, and therefore, a smaller amplitude than the main lobe. Another example is a bell-shaped or Gaussian distribution whose one main lobe has a gradually tapered beam skirt.

When scanning over the surface of the specimen, the beam skirt of the incident laser beam may reach a particle or defect (e.g., on the order of one to several microseconds) before the particle or defect is reached by the main beam. For example, most particles or defects on the surface of a specimen will be significantly smaller than the spot size of the laser beam. This enables the beam skirt to reach a particle or defect before it is reached by the main beam. As the incident laser beam is scanned over the surface of the specimen, the amount of light scattered from the specimen (i.e., the scatter power) will change depending on what part of the beam is covering the particle or defect. Assume, for example, that the high power density main beam covers a relatively smooth surface of the specimen when the low power density beam skirt reaches a large particle or defect. Because the amount of light scattered from relatively smooth surfaces is typically a lot smaller than the scatter attributed to large particles or defects, the amount of scatter power attributed to the main beam portion may be considered negligible. As such, a significant increase in the scatter power may indicate that the beam skirt has reached a large particle or defect. In other words, the presence of large particles or defects may be detected at a nearby location by monitoring the scatter levels from the low power density beam skirt.

If the scatter levels from the beam skirt are substantially greater than or equal to the safe scatter threshold (in step 310), the incident laser beam may be reduced to a second power level, lower than the first (in step 314). As noted above, the second power level (referred to as the "safe" power level) may typically range between about 1% to about 50% of the first power level (referred to as the "full" power level), and in a preferred embodiment, may be about 10% of the full power level. If the scatter levels from the beam skirt are less than the safe scatter threshold (in step 310), the first power level will be maintained to enable smaller features to be detected and to preserve detection sensitivity.

In some cases, the method may end (in step 318), if the surface inspection scan is complete (in step 316). Otherwise, the scanning process may continue (in step 320) so that the nearby location becomes the current location. The method continues to monitor the beam skirt scatter levels while the incident laser beam moves over the defect. When the scatter levels fall back below the safe scatter threshold (in step 310), indicating that the high density center of the beam (i.e., the main beam) has passed the defect, the first power level will be restored (in step 312) to continue inspecting the specimen for small defects.

By using a fast laser power attenuator, such as those described above and shown in FIGS. 7 and 8, the systems and methods described herein may easily switch between high and low power levels before the main beam reaches the nearby location. For example, beam skirt scatter levels may be used to indicate the presence of a large defect at a nearby location several microseconds before the main beam reaches that location. Due in part to the relatively fast response (e.g., on the order of a few nanoseconds to a few microseconds) of laser power attenuator 26, the present invention is able to reduce the incident beam power level before the main beam reaches the defect by monitoring the beam skirt scatter levels. By dynamically decreasing the power level while scanning large particles, and increasing the power level once the particle is scanned, the present invention reduces thermal damage to large particles, while maintaining system throughput and sensitivity.

Further modifications and alternative embodiments of various aspects of the invention may be apparent to those skilled in the art in view of this description. For example, methods and systems for extending the detection range of an inspection system are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An inspection system, comprising:
    an illumination subsystem for directing light to a specimen at a first power level;
    a detection subsystem for detecting light scattered from the specimen; and
    a power attenuator subsystem for dynamically altering the power level directed to the specimen between at least the first power level and a second power level based on a determination of whether the scattered light detected from the specimen is above or below a predetermined threshold level, wherein the predetermined threshold level is selected to minimize thermal damage caused when the light directed to the specimen is absorbed and inadequately dissipated by a feature on the specimen, and wherein the predetermined threshold level is based on an incident power density associated with onset of thermal damage inflicted on a feature of certain size.

2. The inspection system as recited in claim 1, wherein the power attenuator subsystem comprises a light source for providing the light directed to the specimen.

3. The inspection system as recited in claim 2, wherein the light source is selected from a group of laser-based sources comprising: a diode laser, a helium neon laser, an argon laser, a solid state laser and a diode pumped solid state (DPSS) laser.

4. The inspection system as recited in claim 2, wherein the light source is selected from a group of non-laser-based sources comprising: an Arc lamp, a Mercury high pressure lamp, a Mercury low pressure lamp, an LED array, and a light bulb.

5. The inspection system as recited in claim 2, wherein the power attenuator subsystem further comprises a laser power attenuator arranged between the light source and the specimen, and wherein the laser power attenuator is configured to:
- maintain the light directed to the specimen at the first power level, if the detected scattered light remains below the predetermined threshold level;
- reduce the light directed to the specimen to the second power level, which is less than the first, if the detected scattered light exceeds the predetermined threshold level; and
- increase the light directed to the specimen back to the first power level, if the detected scattered light falls back below the predetermined threshold level.

6. The inspection system as recited in claim 5, wherein the power attenuator subsystem further comprises a laser power controller coupled between the detection subsystem and the laser power attenuator, wherein the laser power controller is configured to:
- continuously monitor the detected scattered light to determine whether the detected scattered light is above or below the predetermined threshold level; and
- instruct the laser power attenuator to provide the light directed to the specimen at either the first power level or the second power level, based on the determination made by the laser power controller.

7. The inspection system as recited in claim 1, wherein the predetermined threshold level is selected from a group of incident laser power densities ranging from about 1 kW/cm$^2$ to about 1000 kW/cm$^2$.

8. The inspection system as recited in claim 1, wherein the second power level comprises a percentage of the first power level, and wherein the percentage is selected from a group comprising about 1% to about 50%.

9. The inspection system as recited in claim 8, wherein the second power level is substantially equal to about 10% of the first power level.

10. The inspection system as recited in claim 8, wherein the inspection system is configured to detect features of relatively small size by directing the light to the specimen at the first power level.

11. The inspection system as recited in claim 10, wherein the inspection system is further configured to detect features of relatively larger size, without inflicting the thermal damage on those features, by directing the light to the specimen at the second power level, rather than the first.

12. The inspection system as recited in claim 1, wherein the power attenuator subsystem utilizes more than one predetermined threshold level for dynamically selecting an appropriate power level to be directed to the specimen, and wherein the appropriate power level is selected from three or more different power levels available for use.

13. A method for inspecting a specimen, the method comprising:
- directing light to the specimen at a first power level;
- scanning the light over a surface of the specimen, wherein during said scanning, the method comprises:
  - detecting light scattered from the specimen;
  - reducing the light directed to the specimen to a second power level, if the detected light exceeds a predetermined threshold level, wherein the predetermined threshold level is selected to minimize thermal damage caused when the light directed to the specimen is absorbed and inadequately dissipated by a feature on the specimen, and wherein the predetermined threshold level is based on an incident power density associated with onset of thermal damage inflicted on a feature of certain size; and
- detecting features, defects or light scattering properties of the specimen using the detected light scattered from the specimen.

14. The method as recited in claim 13, wherein if the predetermined threshold level is exceeded, the method further comprises increasing the light directed to the specimen back to the first power level, if the detected scattered light falls back below the predetermined threshold level during said scanning.

15. The method as recited in claim 14, wherein the step of directing the light to the specimen supplies the light to the surface of the specimen with a power density distribution that peaks near the middle of the distribution and tapers off near the edges of the distribution, and wherein the middle of the distribution is referred to as the main beam and the edges of the distribution are referred to as the beam skirt.

16. The method as recited in claim 15, wherein the power density distribution comprises a main lobe with at least one side lobe on each side of the main lobe, the side lobes being smaller in power density than the main lobe.

17. The method as recited in claim 15, wherein the power density distribution comprises a Gaussian distribution.

18. The method as recited in claim 15, wherein the step of detecting the light enables the light directed to the specimen to be reduced to the second power level before the main beam reaches a relatively large feature on the specimen, the relatively large feature being susceptible to the thermal damage if the main beam were supplied thereto at the first power level.

19. The method as recited in claim 18, wherein during said scanning, the method further comprises:
- monitoring light scattered from the specimen; and
- using the monitored light to select the predetermined threshold level to be used for selecting an appropriate power level to be directed to the specimen.

* * * * *